United States Patent
Ben-Shalom et al.

(10) Patent No.: US 9,034,348 B2
(45) Date of Patent: *May 19, 2015

(54) INJECTABLE CHITOSAN MIXTURES FORMING HYDROGELS

(71) Applicant: CHI2GEL Ltd., Tel Aviv (IL)

(72) Inventors: Noah Ben-Shalom, Tel Aviv (IL); Zvi Nevo, Herzlia (IL); Abraham Patchornik, Nes Ziona (IL); Dror Robinson, Kfar-Shmuel-Doar-Na Shimshon (IL)

(73) Assignee: Chi2Gel Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,268

(22) Filed: Mar. 14, 2013

(65) Prior Publication Data

US 2013/0244972 A1 Sep. 19, 2013

Related U.S. Application Data

(60) Continuation-in-part of application No. 13/438,542, filed on Apr. 3, 2012, now abandoned, which is a division of application No. 12/155,916, filed on Jun. 11, 2008, now Pat. No. 8,153,612, which is a (Continued)

(51) Int. Cl.
*A61K 9/00* (2006.01)
*A61K 47/36* (2006.01)
(Continued)

(52) U.S. Cl.
CPC ............. *A61K 47/36* (2013.01); *A61L 26/0023* (2013.01); *A61K 31/738* (2013.01); *A61L 27/20* (2013.01);

(Continued)

(58) Field of Classification Search
CPC ...................................... A01N 43/04
USPC ............................................. 424/400
See application file for complete search history.

(56) References Cited

U.S. PATENT DOCUMENTS 5,770,712 A 6/1998 Roy
5,851,229 A 12/1998 Lentz
(Continued)

FOREIGN PATENT DOCUMENTS

JP H10-309287 11/1998
JP 2005-132737 5/2005
(Continued)

OTHER PUBLICATIONS

Aiba (1991) Studies on chitosan: 3. Evidence for the presence of random and block copolymer structures in partially N-acetylated chitosans. Int J Biol Macromol 13(1): 40-4.

(Continued)

*Primary Examiner* — Benjamin Packard
(74) *Attorney, Agent, or Firm* — Winston & Strawn LLP

(57) ABSTRACT

A chitosan composition which forms a hydrogel at near physiological pH and 37° C., comprising at least one type of chitosan having a degree of acetylation in the range of from about 30% to about 60%, and at least one type of chitosan having a degree of deacetylation of at least about 70% is disclosed. Further disclosed is a chitosan composition which forms a hydrogel at near physiological pH and 37° C., that includes at least one type of chitosan having a degree of deacetylation of at least about 70% and a molecular weight of from 10-4000 kDa, and at least one type of a chitosan having a molecular weight of from 200-20000 Da. Further disclosed are methods of preparation and uses of the chitosan compositions.

26 Claims, 17 Drawing Sheets

Room Temperature

Body Temperature

Related U.S. Application Data continuation-in-part of application No. PCT/IL2007/001530, filed on Dec. 11, 2007.

(60) Provisional application No. 60/924,582, filed on May 21, 2007, provisional application No. 60/873,931, filed on Dec. 11, 2006.

(51) Int. Cl.

| | |
|---|---|
| A61L 26/00 | (2006.01) |
| A61K 31/738 | (2006.01) |
| A61L 27/20 | (2006.01) |
| A61L 27/52 | (2006.01) |
| A61L 27/60 | (2006.01) |
| A61K 8/73 | (2006.01) |
| A61Q 19/00 | (2006.01) |
| A61K 9/06 | (2006.01) |
| A61K 8/04 | (2006.01) |
| C08J 3/075 | (2006.01) |
| C08L 5/08 | (2006.01) |
| A61L 27/38 | (2006.01) |
| A61Q 19/08 | (2006.01) |

(52) U.S. Cl.
CPC ............... *A61L 27/52* (2013.01); *A61L 27/60* (2013.01); *A61K 8/736* (2013.01); *A61Q 19/00* (2013.01); *A61K 9/0009* (2013.01); *A61K 9/0014* (2013.01); *A61K 9/0024* (2013.01); *A61K 9/06* (2013.01); *A61K 8/042* (2013.01); *C08J 3/075* (2013.01); *C08L 5/08* (2013.01); *A61K 2800/594* (2013.01); *A61K 2800/91* (2013.01); *A61L 2400/06* (2013.01); *C08J 2305/08* (2013.01); *A61K 2800/805* (2013.01); *A61L 27/3804* (2013.01); *A61L 26/008* (2013.01); *A61Q 19/08* (2013.01)

(56) References Cited

U.S. PATENT DOCUMENTS

| | | |
|---|---|---|
| 6,344,488 B1 | 2/2002 | Chenite |
| 2005/0208122 A1 | 9/2005 | Allen |
| 2006/0127873 A1 | 6/2006 | Hoemann |

FOREIGN PATENT DOCUMENTS

| | | |
|---|---|---|
| WO | 99/07416 | 2/1999 |
| WO | 01/10421 | 2/2001 |
| WO | 03/011912 | 2/2003 |
| WO | 03/037935 | 5/2003 |
| WO | 2004/068971 | 8/2004 |
| WO | 2004/069230 | 8/2004 |
| WO | 2005/097871 | 10/2005 |
| WO | 2006/067626 | 6/2006 |
| WO | 2006/134614 A1 | 12/2006 |
| WO | 2008/072230 | 6/2008 |
| WO | 2010/109460 | 9/2010 |

OTHER PUBLICATIONS

Aiba (1994) Preparation of N-acetylchitooligosaccharides from lysozymic hydrolysates of partially N-acetylated chitosans. Carbohydrate Research 261(2): 297-306.
Berger et al., (2005) Pseudo-thermosetting chitosan hydrogels for biomedical application. Int J Pharm 288(2): 197-206.
Calvo et al., (1997) Evaluation of cationic polymer-coated nanocapsules as ocular drug carriers. International Journal of Pharmaceutics 153(1): 41-50.
Chenite et al., (2000) Novel injectable neutral solutions of chitosan form biodegradable gels in situ. Biomaterials 21 (21): 2155-61.
Felt et al., (1999) Topical use of chitosan in ophthalmology: tolerance assessment and evaluaton of precorneal retention. Int J Pharm 180(2): 185-93.
Felt et al., (2000) Chitosan as tear substitute: a wetting agent endowed with antimicrobial efficacy. J Ocul Pharmacol Ther 16(3): 261-70.
He et al., (1998) In vito evaluation of the mucoadhesive properties of chitosan microspheres. Int J Pharm 166(1): 75-88.
Hoemann et al., (2005) Chitosan-glycerol phosphate/blood implants improve hyaline cartilage repair in ovine microfracture defects. J Bone Joint Surg. JBJS.ORG vol. 87(12): 2671-86.
Jiang et al., (2005) Biodegradable hyaluronic acid/n-carboxyethyl chitosan/protein ternary complexes as implantable carriers for controlled protein release. Macromol Biosci 5(12): 1226-33.
Junginger and Verhoef (1998) Macromolecules as safe penetration enhancers for hydrophilic drugs—a fiction? PSTT 1: 370-6.
Katsube et al., (2000) Repair of articular cartilage defects with cultured chondrocytes in Atelocollagen gel. Comparison with cultured chondrocytes in suspension. Arch Orthop Trauma Surg 120(3-4): 121-7.
Lamarque et al., (2005) Physicochemical behavior of homogeneous series of acetylaed chitosans in aqueous solution: role of various structural parameters. Biomacromolecules 6(1): 131-42.
Lee et al., (2006) Preparation of chitosan microfibres using electro-wet-spinning and their electroactuation properties: Smart Mater Struct 15(2): 607-11.
Liu et al., (2001) Antibacterial action of chitosan and carboxymethylated chitosan. J Appl Polym Sci 79(7): 1324-35.
Mi et al., (2000) Synthesis and characterization of a novel chitosan-based newark prepared using naturally occurring crosslinker. J Polym Sci A: Polym Chem 38(15): 2804-14.
Milot et. al., (1998) Influence of physicochemical and structural characteristics of chitosan flakes on molybdate sorption. J Appl Polymer Sci 68(4): 571-80.
Molinaro et al., (2002) Biocompatibility of thermosensitive chitosan-based hydrogels: an in vivo experimental approach to injectable biomaterials. Biomaterials 23(13): 2717-22.
Muzzarelli (1997) Human enzymatic activities related to the therapeutic administration of chitin derivatives. Cell Mol Life Sci 53(2): 131-40.
Ogawa and Yui, (1993) Crystallinity of Partially N-Acetylated Chitosans Biosci. Biotechnol. Biochem 57(9): 1466-9.
Patashnik et al., (1997) Preparation and evaluation of chitosan micospheres containing bisphosphonates. J Drug Target 4(6): 371-80.
Patchornik et al., (2012) Chitosan-hyaluronate hybrid gel intraarticular injection delays osteoarthritis progression and reduces pain in a rat meniscectomy model as compared to saline and hyaluronate treatment. Adv Orthop 2012: 979152.
Roughley et al., (2006) The potential of chitosan-based gels containing intervertebral disc cells for nucleus pulposus supplementation. Biomaterials 27: 388-96.
Shigemasa et al., (1994) Enzymatic degradation of chitins and partially deacetylated chitins. Intenational Jounal of Biological Macromolecules 16(1): 43-49.
Song et al., (2001) A phase I/IIa study on intra-articular injection of holmium-166-chitosan complex for the treatment of knee synovitis of rheumatoid arthritis. Eur J Nucl Med 28(4): 489-97.
Ueno et al., (2001) Topical formulations and wound healing applications of chitosan. Adv Drug Delivery Rev 52(2): 105-15.
Yamane et al., (2005) Feasibility of chitosan-based hyaluronic acid hybrid biomaterial for a novel scaffold in cartilage tissue engineering. Biomaterials 26(6): 611-9.

a.
b.

a.

b.

a.
b.

INJECTABLE CHITOSAN MIXTURES FORMING HYDROGELS

FIELD OF THE INVENTION

The present invention, in some embodiments thereof, relates to positively charged polysaccharide hydrogels, and, more particularly, to pH-dependant, thermosensitive polysaccharide hydrogels, aqueous solutions used to form such hydrogels, and methods of preparation and uses thereof.

BACKGROUND OF THE INVENTION

Hydrogels are highly hydrated, macromolecular networks, dispersed in water or other biological fluids.

Hydrogels that exhibit the specific property of increased viscosity with increased temperatures are known as thermosensitive (or thermosetting) hydrogels. Such hydrogels have been shown to have easier application combined with longer survival periods at the site of application as compared to non-thermosensitive hydrogels, and are therefore advantageous as slow-release drug delivery systems.

It is known that thermosensitive hydrogels may be prepared from polymers of natural origin (O. Felt et al. in The Encyclopedia of Controlled Drug Delivery, 1999), such as chitosan, which is a commercially available, inexpensive polymer obtained by partial to substantial alkaline N-deacetylation of chitin, a linear polysaccharide, made of N-acetylglucosamine units, linked via β-1,4 glycosidic bonds. The deacetylation process is generally performed using hot, concentrated, hydroxide solutions, usually sodium hydroxide.

Chitin is a naturally occurring biopolymer, found in the cytoskeleton and hard shells of marine organisms such as crustacea, shrimps, crabs, fungi, etc., and is the third most abundant naturally occurring polysaccharide after cellulose and laminarine. Chitin is chemically inert, insoluble and, has a crystalline structure in the form of flakes, crumbs or tiles.

Chitosan contains free amine ($-NH_2$) groups and may be characterized by the proportion of N-acetyl-D-glucosamine units to D-glucosamine units, commonly expressed as the degree of acetylation (DA) (reciprocal to deacetylation) of the chitin polymer. Both the degree of acetylation, and the molecular weight (MW) are important parameters of chitosan, influencing properties such as solubility, biodegradability and viscosity.

Chitosan is the only positively charged polysaccharide, making it bioadhesive, which delays the release of a medication agent from the site of application (He et. al., 1998; Calvo et. al., 1997), and allows ionic salt interactions with anionic natural compounds such as glycoaminoglycans of the extracellular membrane.

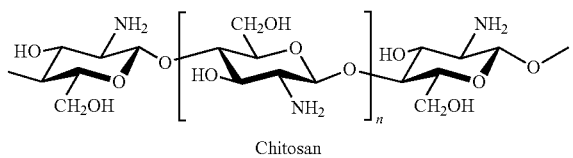

Chitosan

Chitosan is biocompatible, non-toxic, and non-immunogenic, allowing its use in the medical, pharmaceutical, cosmetic and tissue construction fields. For example, topical ocular applications and intraocular injections or transplantation in the vicinity of the retina (Felt et. al., 1999; Patashnik et. al.; 1997; Song et. al., 2001). Moreover, chitosan is metabolized-cleaved by certain specific enzymes, e.g. lysozyme, and can therefore be considered as bioerodable and biodegradable (Muzzarelli 1997, Koga 1998). In addition, it has been reported that chitosan acts as a penetration enhancer by opening epithelial tight-junctions (Junginger and Verhoef, 1998; Kotze et. al., 1999), similar to the action of the enzyme hyaluronidase, the so called "spreading factor". Chitosan also promotes wound-healing, as well as acting as an antiadhesive (preventing pathological adhesions) (Biagini et. al., 1992; Ueno et. al., 2001) and exhibits anti-bacterial, (Felt et. al., 2000; Liu et. al., 2001), anti-fungal effects, and anti-tumor properties.

Considering the remarkable properties of chitosan, there is a growing need for new chitosan hydrogels for use in the growing industries of slow-release of drugs and regenerative medicine.

Hydrogels comprising chitosan are very useful for drug delivery. They may conveniently be administered by local (intra-articular) routes; they are injectable using minimally invasive procedures; drug delivery using hydrogels provides a high level of concentration of the drug directly at the target site; and they minimize adverse systemic effects and toxicity of the drug.

Chitosan microspheres have been developed for the delivery of drugs, in which drug release is controlled by particle size, degree of hydration, swelling ratio or biodegradability of the prepared microspheres. Attempts have been made to develop chitosan microspheres for the delivery of drugs such as anti-cancer drugs, peptides, antibiotic agents, steroids, etc. by cross-linking of chitosan to form a network.

Conventional chitosan cross-linking reactions have involved a reaction of chitosan with dialdehydes, which may have physiological toxicity. Novel chitosan networks with lower cytotoxicity were synthesized using a naturally occurring crosslinker called genipin, which provides bifunctional crosslinking by heterocyclic linking of genipin with chitosan by a nucleophilic attack and the formation of amide linkages (Mi et al., 2000).

The preparation of thermosensitive, neutral solutions based on chitosan/polyol salt combinations has been described by Chenite et al., 2000. These formulations possess a physiological pH and can be held liquid below room temperature for encapsulating living cells and therapeutic proteins; they form monolithic gels at body temperature, without any chemical modification or cross-linking. The addition of polyol salts bearing a single anionic head results in the formation of a gel due to synergistic forces favorable to gel formation, such as hydrogen bonding, electrostatic interactions and hydrophobic interactions. When injected in vivo the liquid formulation turns into gel implants in situ. The system has been used as a container-reservoir for delivery of biologically active growth factors in vivo as well as an encapsulating matrix for living chondrocytes for tissue engineering applications.

Chitosan-glycerol phosphate/blood implants have been shown to improve hyaline cartilage repair in microfracture defects by increasing the amount of tissue and improving its biochemical composition and cellular organization (Hoemann et al., 2005). The microfracture defect is filled with a blood clot inhabited by bone-marrow derived cells that has been stabilized by the incorporation of chitosan. The use of such implants would therefore be expected to result in better integration, improved biochemical properties, and longer durability of the repair tissue.

Uniform submicron chitosan fibers, which may have an important application as artificial muscles, as biosensors, or as artificial organ components, may be prepared by electro-wet-spinning technology (Lee et al. 2006).

Chitosan-based gels have been shown to turn into and serve as scaffolds for the encapsulation of invertebral disc (IVD) cells (Roughley et al., 2006), by entrapping large quantities of newly synthesized anionic protcoglycan. Such gels would therefore be a suitable scaffold for cell-based supplementation to help restore the function of the nucleus pulposus structural region during the early stages of IVD degeneration. A denser, fibrillar collagen fabric may serve as an annulus fibrosis structural substitute, allowing colonization with endogenous cells.

Collagen gel has previously been shown to be useful for repair of articular cartilage defects with cultured chondrocytes embedded in the gel (Katusbe et al., 2000). More recently, chitosan hydrogels have been shown to be useful for cartilage regeneration and prevention of knee pain associated with acute and chronic cartilage defects.

Recently, temperature-controlled pH-dependant formation of ionic polysaccharide gels, such as chitosan/organo-phosphate aqueous systems, has been described (WO 99/07416 and U.S. Pat. No. 6,344,488). While chitosan aqueous solutions are pH-dependent gelating systems, the addition of a mono-phosphate dibasic salt of polyol or sugar to a chitosan aqueous solution leads to further temperature-controlled pH-dependant gelation. Solid organo-phosphate salts are added and dissolved at low temperature within 0.5 to 4.0% w/v chitosan in aqueous acidic solutions. Aqueous chitosan/organo-phosphate solutions are initially stored at low temperatures (4° C.), then endothermally gelated within the temperature range of 30 to 60° C. Chitosan/organo-phosphate solutions rapidly turn into gels at the desired gelation temperature.

An advanced clinical product of such chitosan hydrogels is a hydrogel produced by BioSyntech. The thermosensitive chitosan hydrogel of BioSyntech is prepared by neutralizing a commercial chitosan, having a degree of deacetylation of about 80-90%, with mono-phosphate dibasic salts of polyols, particularly β-glycerophosphate (β-GP). Addition of β-GP to chitosan enables the pH to be increased up to about 7 without chitosan precipitation, and to form a hydrogel at that pH, at physiological temperature.

A chitosan hydrogel (BST-CarGel™) is produced by Bio-Syntech, which fills cartilage defects and provides an optimal environment for cartilage repair. The chitosan plasticizer mixture is delivered within a debrided cartilage defect following microfracture, using the patient's own blood as a sole source of biological ingredients. The mixture fills the defect and solidifies in situ within 8-12 minutes, providing an effective scaffold for cartilage regeneration. Healthy chondrocytes then migrate from the deep inner bone through the microfracture pores and repopulate the gel-filled lesion.

A second BioSyntech chitosan hydrogel, BST-DermOn™, may be used as a topical therapy for stimulating and supporting wound healing. The product acts as a mucoadhesive barrier and can seal the wound and maintain a moist environment while continuing to allow gas exchange.

A further BioSyntech chitosan hydrogel, BST-InPod™, is intended for treatment of heel pain. This is an injectable product which is intended to permanently restore comfort of plantar fat pads by integrating with the patient's own pad fat and restoring biomechanical cushioning properties and comfort.

These products, however, also exhibit some limitations. The BioSyntech products comprising commercially available chitosan, having a degree of acetylation of about 15-20% DA, are believed to exert an undesired slower degradation rate. Furthermore, chitosan has limited ability to mix with and encapsulate cells at physiological pH of 7.4 to form a three-dimensional scaffold.

The BioSynthech family of hydrogels has limited degradation rates and the formation of such hydrogels requires the presence of glycerophosphate or similar plasticizing salts. Glyerophosphate is a negatively charged molecular entity that can react with positive charges of bioactive components, leading to their precipitation, or to the disturbance of their release from the hydrogel. Therefore, the presence of glycerophosphate may decrease the range of drugs with which chitosan/glycerophosphate hydrogels can be used.

Further, the modulation of the properties of the hydrogel, such as gelation time and viscosity, depends on the concentration of glycerophosphate, and is therefore limited by the solubility of glycerophosphate. In particular, a high concentration of glycerophosphate is required to have a low gelation time, avoiding the rapid elimination of the hydrogel after its administration. However, a high concentration of glycerophosphate also decreases the viscosity of the hydrogel. Therefore, the gelation time has to be balanced with the consistency of the hydrogel, and it is not possible to obtain hydrogels that have both low gelation time and high viscosity, which would be a desirable combination of characteristics. Also, a too high concentration of glycerophosphate may induce the precipitation of the hydrogel at its administration site.

Further, thermosensitive chitosan/glycerophosphate gels were found to be turbid, thus rendering their use inappropriate for particular applications such as ocular or topical administrations.

Multiple interactions are responsible for the solution/gel transition: the increase of chitosan interchain hydrogen bonding, as a consequence of the reduction of electrostatic repulsion, due to the basic nature and action of the salt, and the chitosan-chitosan hydrophobic interactions which should be enhanced by raising the pH. The gelation process that occurs upon increasing the temperature, predominantly originates due to the strengthening of the chitosan hydrophobic attractions, also shown in the presence of the glycerol moiety (serving as a plasticizer) and chitosan. At low temperatures, strong chitosan-water interactions, protects the chitosan chains from aggregation. Upon heating, sheaths of water molecules are removed, allowing the association of aligned chitosan macromolecules. Furthermore, electrostatic forces may decrease upon raising the temperature, and the hydrophobic interactions are expected to have a major contribution to the gelation of the chitosans mixture.

Transparent chitosan/glycerophosphate hydrogels have been prepared, requiring modification of deacetylation of chitosan by reacetylation with acetic anhydride. The use of previously filtered chitosan, dilution of acetic anhydride and reduction of temperature has been shown to improve efficiency and reproducibility (Berger et al., 2004).

Turbidity of chitosan/glycerophosphate hydrogels has been shown to be modulated by the degree of deacetylation of chitosan and by the homogeneity of the medium during reacetylation, which influences the distribution mode of the glucose amine monomers. The preparation of transparent chitosan/glycerophosphate hydrogels therefore requires a homogeneously reacetylated chitosan with a degree of deacetylation between 30 and 60%.

It has been found that reacetylation of commercial chitosan to produce homogenously acetylated chitosans having a degree of acetylation of from about 30% to about 60%, greatly increases the solubility of the chitosan in water and body fluids at physiological pH, without the need to use glycerol phosphate. Such chitosans produce clear transparent gels, which may be used for cell encapsulation (WO 05/097871 to Berger et al).

Homogeneous reacetylation of chitosan on one hand has the effect of increasing the number of hydrophobic sites by replacing amine groups with acetyl groups, but on the other hand the crystalline structure that makes chitosan tend to fold is highly reduced cumulating in increased solubility of the chitosan. Reacetylation prevents refolding of the polymer, maintaining the straight chain, and thus preventing the pH-related decrease in solubility.

An example of commercial chitosan which may be used in the preparation of reacetylated chitosan is a chitosan of pharmaceutical grade and high MW obtained from Aldrich Chemical, Milwaukee, USA, having a MW of 1100 kDa as determined by size exclusion chromatographic method reported by O. Felt, et al. in Int. J. Pharm. 180, 185-193 (1999) and a deacetylation degree DD of 83.2% as measured by UV method reported by R. A. Muzarelli et al. in "Chitin in Nature and Technology", Plenum Press, New York, 385-388, (1986).

However, any commercial chitosan having a deacetylation degree of 80 to 90% and a molecular weight not smaller than 10 kDa may be used. The acidic medium used for dissolving commercial chitosan may be for example acetic acid and the acidic solution of chitosan obtained after solubilization of chitosan may be then diluted with an alcohol, for example methanol.

Generally, commercially available chitosan is industrially prepared by deacetylation of dry chitin flakes (Muzzarelli, 1986). Deacetylation preferentially occurs in the amorphous zones of the chitin molecules at the surface of the flakes, resulting in non-homogeneous monomers with variable block size of deacetylated-units distribution (Aiba, 1991). In comparison, reacetylated chitosan under homogeneous conditions, adopts a random distribution of deacetylated monomers, which induces a decrease of the crystallinity of chitosan and in turn increases its solubility (Aiba, 1991, 1994; Ogawa and Yui, 1993; Milot et. al., 1998).

The suitability of polymeric hydrogels for an application is dictated by their biocompatibility, mechanical integrity, speed and reversibility of gel formation at physiological pH, and their low weight and extended lifetime. However, very little control is possible over various important properties of known chitosan hydrogels, such as strength, rate of degradation, and release profile.

WO 10/109,460 to one of the inventors of the present inventors discloses expandable element comprising an injectable filler which comprises chitosans.

WO 03/011912 teaches a process of preparing chitosan in which in the heterogeneous deacetylation reaction of chitin, the latter is first subjected to a prolonged low temperature alkaline swelling stage. The produced chitosan thus may be obtained with a more random distribution of residual N-acetyl groups along the polymeric chains. The produced chitosan has a controllable degree of deacetylation, degree of depolymerization, and hence degree of water-solubility at physiological pH.

WO 2004/069230 teaches a pharmaceutical composition which comprises a chitosan having an acetylation degree ($F_A$) of from 0.25 to 0.80 (e.g., 0.3 to 0.6 or 0.33 to 0.55), which acts as a release sustaining or monoadhesive agent, and a physiological active agent. Some embodiments of WO 2004/069230 relate to a mixture of two or more chitosans having different acetylation degrees. Such mixtures preferably include chitosans having an acetylation degree higher than 0.25, but some are described as including one chitosan having an $F_A$ value of from 0.25 to 0.80 and one chitosan having an $F_A$ value below 0.25, for example, 0.05 to 0.19. The preparation of compositions having such a mixture of chitosans, however, has not been described in this publication.

The chitosans utilized in the compositions taught in WO 2004/069230 may have a weight average MW within a very broad range, and a very broad concentration range. The taught compositions are powdered compositions, designed for oral administration.

WO 2004/068971 teaches foodstuffs comprising a nutritional food substance and a chitosan having an acetylation degree ($F_A$) of from 0.25 to 0.80, or a mixture of chitosans, as described in WO 2004/069230. The compositions and products taught in these publications are not designed so as to form a gel upon administration to a subject via injection.

SUMMARY OF THE INVENTION

The present inventors have found that a composition comprising at least two different types of chitosans, wherein the different types are classified according to their degree of acetylation/deacetylation and optionally according to the level of homogeneity of the acetylated units, provides a hydrogel in which a greater degree of control over various physical, chemical and pharmacokinetic properties is possible, particularly as compared to hydrogels comprising a single type of chitosan.

The disclosed hydrogel composition is formed under physiological conditions, namely, physiological pH and temperature, and can thus be utilized in a myriad of applications, particularly medical applications such as tissue regeneration, treatment of osteoarthritis, as a lubricant, food additive, and the like.

The present invention provides a pH- and temperature-dependant composition for formation of a polysaccharide hydrogel at physiological conditions. According to one aspect, the present invention provides a chitosan composition which forms a hydrogel at near physiological pH and at 37° C., comprising at least one acetylated chitosan having a degree of acetylation in the range of from about 30% to about 60%, and at least one deacetylated chitosan having a degree of deacetylation that is about 70% to about 95%, the composition being in the form of an aqueous solution at neutral pH, wherein the ratio of said acetylated chitosan to said deacetylated chitosan in the composition is in the range of 1:1 to 4:1.

According to one embodiment, the chitosan composition further comprising at least one negatively charged polysaccharide. According to another embodiment, the negatively charged polysaccharide is hyaluronic acid.

According to yet another embodiment, the chitosan composition further comprising acetylglucosamine oligomers. According to yet another embodiment, the acetylglucosamine oligomers comprise Tri-N-acetyl-glucosamine. According to yet another embodiment, the acetylglucosamine oligomers are present in the composition at a concentration of between 0.05% to 10% w/v.

According to yet another embodiment, the chitosan composition further comprising a cross-linking agent in an amount sufficient to accelerate gelation of the chitosan composition. According to yet another embodiment, the cross-linking agent is capable of cross-linking the amine or hydroxyl residues of the chitosans. According to yet another embodiment, the amount of the cross linking agent is in the range of between 0.1% to 2% w/v. According to yet another embodiment, the cross-linking agent is added to the chitosan composition prior to introducing said chitosan composition into a site in vivo. According to yet another embodiment, the cross-linking agent is genipin.

According to another aspect, the present invention provides a process for preparing a stable pH-dependent and temperature-dependent chitosan hydrogel composition comprised of at least one acetylated chitosan having a degree of acetylation of from about 30% to about 60%, and at least one deacetylated chitosan having a degree of deacetylation that is about 70% to about 95%, which process comprises:

a) dissolving said acetylated chitosan and said deacetylated chitosan in an acidic aqueous solution at a temperature between 0° C. to 10° C., to thereby form a composite solution, wherein the ratio of said acetylated chitosan and said deacetylated chitosan in said composite solution is in the range of 1:1 to 4:1;

b) adjusting the pH of said composite solution to a value of 6.6 to 7.4 at a temperature between 0° C. to 10° C.; and c) increasing at least one of the temperature of said composite solution to about 37° C. and/or raising the pH to physiological pH.

According to one embodiment, the process further comprising adding a negatively charged polysaccharide to the composition before step c). According to another embodiment, the polysaccharide is hyaluronic acid.

According to yet another embodiment, the process further comprising adding acetylglucosamine oligomers to the composition.

According to yet another embodiment, the process further comprising adding a cross-linking agent in an amount sufficient to accelerate gelation of the chitosan composition, wherein the cross-linking agent is added to the composition prior to introducing said chitosan composition into a site in vivo. According to yet another embodiment, the cross-linking agent is genipin.

According to yet another aspect, the present invention provides a hydrogel chitosan composition formed by the process of the invention.

According to yet another aspect, the present invention provides a method of treating medical condition in a subject in need thereof, comprising applying into a site of the medical condition a chitosan composition comprising at least one acetylated chitosan having a degree of acetylation in the range of from about 30% to about 60%, and at least one deacetylated chitosan having a degree of deacetylation that is about 70% to about 95%, the composition being in the form of an aqueous solution at neutral pH, wherein the ratio of said acetylated chitosan to said deacetylated chitosan in the solution is in the range of 1:1 to 4:1.

According to one embodiment, the medical condition is selected from the group consisting of: osteoarthritis, fracture repair, bone structural support, cartilage repair, intervertebral disc repair, meniscal repair, bone reconstruction, bone filling and synovial fluid replacement.

According to yet another aspect, the present invention provides a kit for producing a chitosan hybrid hydrogel, comprising:

(i) a container containing a chitosan composition comprising at least one acetylated chitosan having a degree of acetylation in the range of from about 30% to about 60%, and at least one deacetylated chitosan having a degree of deacetylation that is about 70% to about 95%, wherein the ratio of said acetylated chitosan to said deacetylated chitosan in the solution is in the range of 1:1 to 4:1;

(ii) a container containing a cross-linking agent in an amount sufficient to accelerate gelation of the chitosans; and (iii) instructions for preparing the chitosan hybrid hydrogel.

According to one embodiment, the container containing a chitosan composition further comprises a negatively charged polysaccharide. According to another embodiment, the polysaccharide is hyaluronic acid.

According to yet another embodiment, the container containing a chitosan composition further comprises acetylglucosamine oligomers. According to yet another embodiment, the acetyl glucosamine oligomers comprise Tri-N-acetyl-glucosamine. According to yet another embodiment, the kit further comprises a container containing a solvent for dissolving the cross-linking agent.

According to another aspect of the present invention there is provided a method for the production of a stable hydrogel which comprises a composition of at least one highly acetylated chitosan having a degree of acetylation of from about 30 to about 60%, and at least one highly deacetylated chitosan having a degree of deacetylation of from about 70%. The method is effected by dissolving at least one highly acetylated chitosan and at least one highly deacetylated chitosan in an acidic aqueous solution, to form a composite solution; adjusting the pH of the composite solution to a value of from 6.5 to 7.2; and increasing the temperature of the composite solution to 37° C. while raising the pH to from 7.0 to 7.6.

The chitosan gel resulting from this mixture of at least two chitosan types may optionally comprise microspheres of chitosan encapsulating a drug and/or electrospun chitosan fibers embedded in the gel.

In some embodiments, the highly acetylated chitosan is either homogenously acetylated or homogenously deacetylated. In some embodiments, the highly deacetylated chitosan is non-homogenously deacetylated.

The highly acetylated chitosan and the highly deacetylated chitosan may optionally each be present at a concentration of from about 0.1% to about 6% w/v of the total composition, and may each have a molecular weight in the range of from about 10 kDa to about 4000 kDa. In some embodiments, the highly acetylated chitosan and the highly deacetylated chitosan are each present at a concentration of from about 0.2% to about 3% w/v of the total composition. Alternatively, the highly acetylated chitosan and the highly deacetylated chitosan are each present at a concentration of from about 0.5% to about 2% w/v of the total composition. In some embodiments, the highly acetylated chitosan and the highly deacetylated chitosan are each present at a concentration of from about 1% to about 1.2% w/v of the total composition.

In some embodiments, the highly acetylated chitosan has a molecular weight of greater than about 200 kDa. In some embodiments, the highly deacetylated chitosan has a molecular weight of greater than about 60 kDa. Alternatively, the highly deacetylated chitosan has a molecular weight of greater than 200 kDa. Further alternatively, the highly deacetylated chitosan has a molecular weight of greater than about 400 kDa.

Further alternatively, the highly deacetylated chitosan has a molecular weight that ranges from 400 kDa to 700 kDa and the highly acetylated chitosan has a molecular weight that ranges from 200 kDa to 250 kDa. Further alternatively, in this embodiment, each of the highly acetylated chitosan and the highly deacetylated chitosan is present at a concentration of from 1% to 1.2% (w/v) of the composition. Further alternatively, the ratio of the highly acetylated chitosan and the highly deacetylated chitosan is 1:1.

The properties of the hydrogel may be controlled by manipulation of the molecular weight, degree of deacetylation and distribution of the deacetylated sites of both the highly acetylated chitosan and the highly deacetylated chitosan. These manipulations will influence the gel properties, such as, for example, the gelation temperature, density or porosity, or the degree of hydration or the degree of hydrophobicity. Alternatively, properties of the hydrogel such as gelation temperature and gelation pH can be controlled by manipulation of the molecular weight, the concentration and ratio of the chitosan types.

Further alternatively, the manipulation comprises manipulation of a feature selected from the group consisting of a molecular weight of each of the highly acetylated chitosan and the highly deacetylated chitosan, a concentration of each of the highly acetylated chitosan and the highly deacetylated chitosan in the composition and a ratio of the highly acetylated chitosan and the highly deacetylated chitosan.

In one embodiment, when a concentration of each of the highly acetylated chitosan and the highly deacetylated chitosan ranges from 1% to 1.2% w/v of the composition and the ratio is 1:1, the hydrogel is formed at near physiological pH. In one embodiment, the highly deacetylated chitosan has a molecular weight of from 400 kDa to 700 kDa and the highly acetylated chitosan has a molecular weight of from 200 kDa to 250 kDa. In one embodiment, when the highly deacetylated chitosan has a molecular weight of at least 2000 kDa and a concentration thereof is 0.5%, and further when the highly acetylated chitosan has a molecular weight of from 200 kDa to 250 kDa and the ratio ranges from 2:1 to 4:1, the hydrogel is formed at the near physiological pH.

The degradation rate of the hydrogel may be further controlled by binding of the lysozyme inhibitor Tri-N-acetylglucosamine to the highly acetylated chitosan.

The chitosan composition may optionally further comprise a negatively charged polysaccharide, such as, for example, an animal- or plant-derived polymer. As a non-limiting example of a plant-derived polymer, the negatively charged polysaccharide may optionally comprise seaweed. Alternatively, the negatively charged polysaccharide may optionally comprise a glycosaminoglycan, such as, for example, hyaluronic acid, chondroitin sulfate, or other acidic polymers such as dextran sulfate. According to one embodiment, the chitosan composition comprises hyaluronic acid. Alternatively, the chitosan composition may comprise other negatively charged substances, such as, for example, phospholipids. A non-limiting example of a phospholipid is phosphatidyl choline.

Further alternatively, the chitosan composition comprises both a glycosaminoglycan and a phospholipid, as described herein. Such a composition is suitable for use as a synovial replacement composition. According to some embodiments, the chitosan composition described herein may further comprise at least one of a drug, a polypeptide and a cell (such as an animal cell or a plant cell).

The composition may further comprise an emulsifier. Optionally, the chitosans and the emulsifier may form nanoparticles. Optionally, the nanoparticles are encapsulated in the hydrogel.

The chitosan composition described herein can be used to form a hydrogel which is beneficially utilized in an application such as, for example, drug delivery, food additive delivery (via oral ingestion), support of cell growth, bone structural support, cartilage repair, tissue reconstruction, wound-healing, production of artificial skin, as a hypolipidemic and hypocholesterolemic agent (for treating hypolipidemia and hypocholesterlimia), formation of artificial kidney membrane, bone filling, soft tissue reconstruction as for heel pain relief for example, anti adhesion in the field of surgery, lubrication, synovial replacement, apophysitis, tendinitis, mesotherapy, burn treatment, and inflammatory arthritis. The chitosan composition which forms the hydrogel can be administered by a route such as injection or endoscopic administration.

The formed hydrogel may optionally be used in the preparation of a biocompatible material for use in the preparation of an implantable device, such as for use in tissue repair, tissue reconstruction, tissue construction, and tissue replacement.

In some embodiments, the anti-adhesion properties of chitosan makes this gel useful as an anti adhesion device in applications such as cardio thoracic surgery and abdominal surgery, for example.

According to some embodiments, the formed hydrogel may optionally be used in the preparation of a drug delivery device or system. The drug delivery device or system may optionally provide slow release of an embedded medication. Non-limiting examples of drugs for use in this system include proteins (such as BSA or hemoglobin) or non-protein agents (such as, for example, ACE-inhibitors or anti inflammatory drugs). The drug delivery system may optionally be an opthalmological drug delivery system due to the transparency of the gel. However the drug delivery system may also optionally be implemented for urological applications such as vesicoureteral reflux and in cosmetic applications such as for example wrinkle treatment.

The drug may also optionally comprise one or more of a mineral, a vitamin, a food additive or natural extract such as a plant derived extract for example. The gel itself, optionally with an active ingredient, may optionally be used as a food additive. In some embodiments, the drug comprises autologous cells, and the system is being for delivering the cells into rotator-cuff tears and/or tendon damage. Such delivering can be performed under ultrasonographic control.

Alternatively, the formed hydrogel may optionally be used for supporting endogenous cells in a three-dimensional gel construct. As a further alternative, the formed hydrogel may optionally be used for embedding exogenous cells with or without added growth factors, as well the cell may provide metabolites such as growth factors. Also alternatively, the hydrogel may optionally be used in the production of a cell-loaded artificial matrix, where the cells are, for example, chondrocytes, fibrochondrocytes, ligament fibroblasts, skin fibroblasts, tenocytes, myofibroblasts, mesenchymal stem cells and keratinocytes.

According to some embodiments, there is provided a chitosan composition comprising nanoparticles containing an active ingredient and encapsulated in a hydrogel comprising at least one type of chitosan having a degree of acetylation in the range of from about 30% to about 60%, and at least one type of chitosan having a degree of deacetylation of at least about 70%, wherein the hydrogel is formed through pH- and temperature-dependant gelation. Optionally, the composition further comprises an emulsifier. Also optionally, the hydrogel forms upon injection to a subject.

According to some embodiments, the chitosan hydrogel may optionally be used as a lubricating agent in such applications such as vaginal atrophy, dry eyes, conjunctivitis sicca, dry nose following upper respiratory infections as well as a general soothing agent for various abrasions. Chitosan gel may also optionally be used as an anti-inflammatory agent in facial diseases such as fibromyalgia by either local injection or external massage.

According to some embodiments, the chitosan hydrogel is used in a method of mesotherapy which is effected by injecting the chitosan composition described herein. Alternatively, the chitosan hydrogel formed from the chitosan composition described herein can be used as a synovial replacement composition, for use in the treatment of, for example, osteoarthritis. Such a synovial replacement composition is described hereinabove.

According to an aspect of some embodiments of the invention there is provided a process of preparing a stable hydrogel which comprises a highly deacetylated chitosan and a highly acetylated chitosan, as described herein. Further, a hydrogel prepared by this process is provided.

According to a further aspect of some embodiments of the present invention there is provided a chitosan composition which forms a hydrogel at near physiological pH and 37° C., the composition comprising at least one type of a highly deacetylated chitosan having a molecular weight of from 10-4000 KDa and a degree of deacetylation of at least 70%, and at least one type of a chitosan having a molecular weight of from 200-20000 Da, the composition being in a form of an aqueous solution.

In some embodiments, the chitosan having a molecular weight of from 200-20000 Da is selected from the group consisting of a highly deacetylated chitosan having a degree of deacetylation of at least 70% and a highly acetylated chitosan having a degree of acetylation of from 30% to 60%.

In some embodiments, a ratio of the chitosan having a molecular weight of from 200-20000 Da and the highly deacetylated chitosan having a molecular weight of from 10-4000 KDa and a degree of deacetylation of at least 70% is higher than 1:1. In some embodiments, the ratio ranges from 2:1 to 20:1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
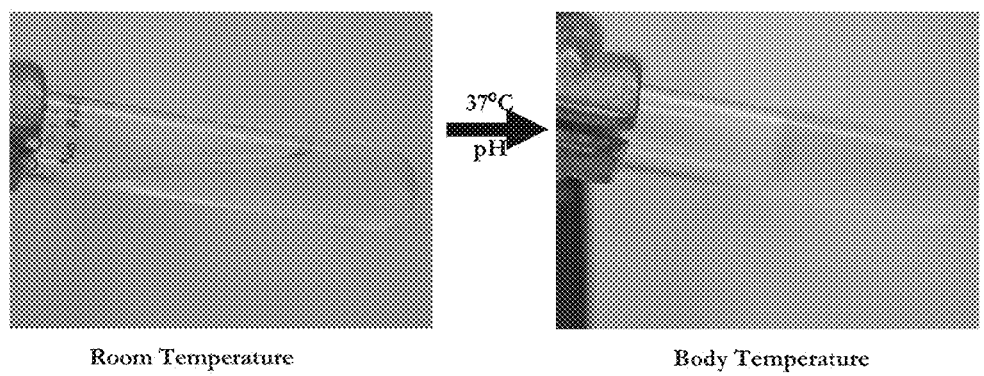
FIG. 1 illustrates the formation of a hydrogel according to some embodiments of the present invention from a liquid composition comprising two different types of chitosan.

The present invention, in some embodiments thereof, relates to positively charged polysaccharide hydrogels, and, more particularly, to pH-dependent, thermosensitive polysaccharide hydrogels formed from an aqueous solution of polysaccharides, to such solutions of polysaccharides and to methods of preparation and uses of pH-dependent, thermosensitive polysaccharide hydrogels.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Chitosans which are deacetylated to a degree of deacetylation (also referred to herein as DD or DDA) of about 70-100% (i.e. degree of acetylation, DA, of up to about 30%), such as commercially available chitosan, are termed herein Type 1 chitosans or chitosans type 1. These chitosans are insoluble at physiological pH, and are poorly recognized by lysozyme. Such chitosans, when utilized in in vivo applications, are typically characterized by relatively slow biodegradation, which, depending on the degree of deacetylation, can last from a few days to a few months. Gels formed by chitosans of this type have a low degree of acetylation, such that the free amine groups participate in dense hydrogen bonds with many hydrophobic interactions.

The degradation rate of chitosans has been shown to be a function of the degree of deacetylation. Degradation of chitosan has an influence on cell proliferation and remodeling.

Highly homogeneously deacetylated or reacetylated chitosans (having degree of acetylation of from about 30% to about 60%) are termed herein type 2 chitosans or chitosans type 2.

Such chitosans are readily digested/degraded by lysozyme, thereby enabling, for example, controlled drug release of a drug encapsulated therein.

If deacetylation degree of chitosan is lower than 30%, the chitosan becomes a polymer close to chitin that is insoluble in acidic conditions and therefore not suitable for use in embodiments of the present invention. At a degree of deacetylation greater than 70%, precipitation of chitosan occurs.

The deacetylation degree of chitosan may be determined by a spectrophotometric method such as described, for example, in the literature by R. A. Muzarelli and R. Richetti [Carbohydr. Polym. 5, 461-472, 1985 or R. A. Muzarelli and R. Richetti in "Chitin in Nature and Technology", Plenum Press 385-388, 1986]. Briefly, in the latter method for example, chitosan is solubilized in 1% acetic acid and the DD is determined by measuring its content of N-acetyl-glucosamine by UV at 200, 201, 202, 203 and 204 nm using N-acetyl-D-glucosamine solutions as standards.

According to one embodiment, the present invention relates to a polysaccharide (chitosan) composition comprising a combination of at least one highly acetylated chitosan (type 2) having a degree of acetylation of from about 30% to about 60%, and at least one highly deacetylated chitosan (type 1), having a degree of deacetylation of at least 70%.

The highly acetylated type 2 chitosans can interact through electrostatic, hydrogen and hydrophobic interactions with the highly deacetylated chitosans type 1. The extent of interaction increases with increasing pH. A composition comprising solutions of both types of chitosan can form a stable gel at physiological pH, without the need for glycerophosphate. The obtained composition is therefore devoid of glycerophosphate.

Thus, the chitosan composition described herein is in a form of an aqueous solution, and forms a hydrogel at physiological conditions (e.g., near physiological pH and 37° C.).

It is noted that the composition described herein can form a gel also at room temperature or at lower temperatures (e.g., 4° C.). Nonetheless, the gel formation at such conditions is slow and may last from a few days to a few months, thus enabling to store and transfer the composition as an aqueous solution.

Type 1 chitosans precipitate at a pH of about 6.5, which is less than physiological pH. Interaction of the highly hydrophobic, homogenous, chitosan type 2 with chitosan type 1 prevents this precipitation of the non-homogenously acetylated type 1 chitosan, by formation of hydrogen and hydrophobic bonds, allowing the formation of a stable solution at pH of about 6.7, and a stable semi-solid hydrogel at about pH 7.0 and above.

The secondary bonds which are formed allow the encapsulation of the non-homogenous chitosan chains and maintain its solubility at pH greater than its pKa value. Generally, such secondary chain interactions are the main molecular forces involved in gel formation (Chenite et. al., 2000; Berger et. al., 2005).

Type 1 chitosans mainly contribute to the stability, strength and rigidity of the gel, and provide slow degradation, while type 2 chitosans contribute to the softness, elasticity and fast solubilization of the gel. The different degradation profiles of type 1 and type 2 chitosans are discussed further in Example 2 below, and are shown in FIG. 2. The type 2 chitosan can be regarded as a "protector" or "coating", which provides a shell around the type 1 chitosan and thus avoids its precipitation and delays its biodegradation.

Furthermore, the type 2 chitosan is recognized by lysozyme. This feature enables to control the degradation rate of a hydrogel formed from the composition described herein.

For example, binding a lysozyme inhibitor to the type 2 chitosan can slow the degradation rate of the formed hydrogel. Alternatively, the type 2 chitosan coating is recognized by the lysozyme and is subjected to faster degradation. See, for example, Example 4 hereinbelow.

According to one embodiment, the chitosan composition of the invention may comprise a cross-linking agent. The cross-linking agent is provided in an amount sufficient to accelerate gelation of the chitosans. According to some embodiments, a sufficient amount of the cross linker is an amount in the range of between 0.1% to 2% w/v, 0.1% to 1.8%, 0.1% to 1.6%, 0.1% to 1.4%, 0.1% to 1.2%, 0.1% to 1%, 0.1% to 0.8%, 0.1% to 0.6%, or 0.1% to 0.4%. According to some embodiments, even lower amounts of the cross linking are sufficient to accelerate gelation. In accordance with those embodiments, the cross linker amount is in the range of between 0.01% to 0.1%, 0.01% to 0.05% or 0.05% to 0.1%.

The term "accelerated gelation" is used to denote that gelation occurs sufficiently rapidly to prevent leakage of the gel formulation after administration of the chitosan mixture composition in vivo. Most notably, rapid gelation is critical for treating intervertebral disc defects to prevent leakage upon removal of the device used for administration. In some cases, a desirable accelerated gelation is one that causes the composition to completely gel in the time between when the cross-linking agent is added and the time that the composition is administered. In some cases, gelation occurs almost instantaneously after the addition of the cross-linking agent. The gelation time can also depend upon the amount of cross-linking agent that is added and a skilled artisan can determine the preferred amounts and types of cross-linking agents for any particular chitosan composition based on routine testing.

The addition of a cross linking agent to the chitosan composition of the invention is also advantageous in that it reduces the inflammatory reaction that may be associated with chitosans injection in vivo. In addition, the cross-linker accelerates gelation of the chitosans and thus avoids linkage of the chitosan composition following injection in vivo.

According to some embodiments, the cross linking agent is added and admixed with the chitosan composition adjacent or prior to injection of the composition of the invention into a site in vivo. According to one embodiment, a site in vivo is a site of a medical condition. According to some embodiments, adjacent or prior to is no more than 1, 2, 3, 4, 5, 6, 7, 8, 9, 10, 15, 20, 25 or 30 minutes. Each possibility represents a separate embodiment of the invention.

According to some embodiments, the cross linker is selected from the group consisting of: divinylsulfon, genipin and glutaraldehyde. Each possibility represents a separate embodiment of the invention. According to one embodiment, the cross-linker is genipin.

According to some embodiments, the chitosan composition further comprises acetylglucosamine oligomers. According to some embodiments, the chitosan composition further comprises N-acetylglucosamine or Oligo-N-acetyl-glucosamine. According to some embodiments, the N-acetylglucosamine may comprise 1-7 monomeric units. The acetylglucosamine oligomers may be present in the composition at a concentration of from 0.05% to 10% w/v, from 0.05% to 9%, from 0.05% to 8%, from 0.05% to 7%, from 0.05% to 6%, from 0.05% to 5%, from 0.05% to 4%, from 0.05% to 3%, from 0.05% to 2%, from 0.05% to 1%, or from 0.05% to 0.5%.

The physical and chemical properties of the hydrogel formed from the described composition are altered by raising or lowering the molecular weight of the chitosans and/or their degree of acetylation, and by the natural acetylation diversity of chitosans from different sources. The properties of the gel can further be controlled by selection of the type of reacetylation (i.e. homogenous or non-homogenous), or by mapping the patterns of distribution of the deacetylated/acetylated sites.

A hydrogel should be regarded as a viscous or semi-solid jelly-like macromolecular network structure that swells in water. The macromolecular network is made up of hydrophilic polymer units that are held together either solely by non-covalent bonds or additionally by a certain amount of covalent bonds. The non-covalent hydrogels, better known as uncross-linked networks, can be soluble in water. The covalent networks, better known as cross-linked hydrogels, are water-insoluble. Crosslinked hydrogels can be prepared from uncrosslinked hydrogels via an intra- or intermolecular chemical reaction of mutually reactive functional groups. If necessary cross-linking can be accomplished via a cross-linking agent as described hereinabove.

Preferably, the highly acetylated chitosan is homogenously acetylated. Further preferably, the highly deacetylated chitosan is non-homogenously deacetylated.

Increasing the molecular weight of the chitosan increases its viscosity, such that the polymer is highly hydrated and highly hydrophobic. A gel formed from such a polymer therefore has an increased strength, and greater water retention. This results in a slow degradation rate, slow drug release, and improved mechanical properties.

Preferably, each of the highly acetylated and highly deacetylated chitosans has a molecular weight of from about 10 kDa to about 4000 kDa. Molecular weight of chitosan may be easily determined by size exclusion chromatography as reported for example by O. Felt, P. Purrer, J. M. Mayer, B. Plazonnet, P. Burri and R. Gurny in Int. J. Pharm. 180, 185-193 (1999). The upper limit of MW is determined by the required ease of administration, which depends on the chosen application.

Increasing the degree of acetylation results in increased hydrophobicity in the range of 0-30% DA, but at higher values, such as 30-60% DA, the polymer begins to become more and more soluble as the amount of DA is increased. Furthermore, increasing the number of acetyl glucosamine groups increases the rate of degradation in the body, due to increased recognition sites for lysozyme. Hence, the rate of release of the hydrogel from the body can be controlled by varying the degree of chitosan acetylation.

Variations in the molecular weight, degree of deacetylation and the distribution of the acetylated sites, concentration and ratio of the two or more chitosans, affect the conditions (pH, temperature etc.) under which gel formation occurs; solubility; biodegradability; degree of reactivity with proteins, active pharmaceutical ingredients or other chemicals; hydrophobicity/hydrophilicity; degree of hydration; as well as biological and biocompatibility properties of the gel, such as effect on cell growth, proliferation and survival, ability of chitosans to function as inflammatory or anti-inflammatory mediators, and the effect of chitosans on acceleration or deceleration of wound healing.

For example, Type 1 chitosans of higher molecular weight have higher hydrophobicity and higher viscosity, resulting in a stronger gel due to higher inter-molecular interactions. Type 1 chitosans of higher DDA have a lower rate of degradation. Type 1 chitosans having higher crystallinity have a lower degradation rate due to the fact that the crystalline form is non-soluble. Hence one skilled in the art can predict properties of the resultant gel mixture, and would therefore be able to create gels having desired characteristics, using unique combinations of the different types of chitosan.

As shown in the Examples section that follows (see, Example 7), variation of the molecular weight of the chitosans used, the concentration thereof and the ratio between the type 1 chitosan and type 2 chitosan affect the conditions at which gel formation occurs. Hence, one skilled in the art can be able to select the appropriate parameters in order to produce a hydrogel under physiological conditions.

Preferably, each of the highly acetylated and the highly deacetylated chitosans is independently present at a concentration of about 0.1% to 6% w/v of the total composition.

In some embodiments, each of the highly acetylated and the highly deacetylated chitosans is independently present at a concentration of about 0.2% to 3% w/v of the total composition.

In some embodiments, each of highly acetylated and the highly deacetylated chitosans is independently present at a concentration of about 0.5% to 2% w/v of the total composition.

In some embodiments, each of highly acetylated and the highly deacetylated chitosans is independently present at a concentration of about 1% to 1.2% w/v of the total composition.

In some embodiments, the ratio between the highly acetylated and the highly deacetylated chitosans is 1:1, such that the above concentrations are for each of the highly acetylated and the highly deacetylated chitosans.

In other embodiments, and depending, for example, on the molecular weight of the chitosans used, as well as their concentration, the ratio can be 2:1, 3:1 and even 4:1. Also contemplated are ratios such as 1.1:1, 1.2:1, 1.5:1 1.8:1, and any other ratio in the range of from 1:1 to 4:1. The ratios of the chitosans are ratios of w/v %.

In general, it can be assumed that increasing the MW of any of the chitosans used for forming the hydrogel, and particularly the type 1 chitosan, allows decreasing its concentration and vise versa, decreasing the MW of the chitosan requires increased concentration thereof, in order to form a hydrogel.

The composition described herein offers greater possibility of controlling the properties of the formed hydrogel, including, for example, the hydrogel strength, rate of degradation, and release rate, as compared to the Chitosan/βGP based hydrogel patented by BioSyntech, and extends the possibilities of controlling the gel's properties, and tailoring them to the needs of a much wider range of chemical and physical uses.

The hydrogel of the present invention may further comprise a third chitosan, selected from either type 1 or type 2, having a different molecular weight or degree of deacetylation, thus extending control over the resultant hydrogel.

The polysaccharide hydrogel according to the present invention may optionally comprise a hybrid of chitosan with a negatively charged substance. Such a substance can be, for example, a negatively charged polysaccharide, such as a glycosaminoglycan, for example, hyaluronic acid or chondroitin sulfate. It should be understood that hyaluronic acid is interchangeable with hyaluronate.

Such a substance can also be a phospholipid. A hybrid with a phospholipid is highly beneficial for use as a synovial replacement in osteoarthritis treatment, as it lowers the friction between cartilage surfaces (see, Example 6 below).

In some embodiments, the chitosan composition described herein further comprises both a glycosaminoglycan and a phospholipid.

Thus, different compositions and mixtures based on these two types of chitosans may be used to provide semi-solid hydrogels with suitable properties for a wide range of applications. Exemplary applications include, but are not limited to drug delivery systems e.g. for slow release of agents or medications, scaffolding of various consistencies, including gels for supporting cell growth or bone structural support; cartilage repair; tissue reconstruction; in wound-dressings, promoting scar free healing and macrophage activation; for production of artificial skin; as a hypolipidemic and hypocholesterolemic agent; as an artificial kidney membrane; for bone filling; and heel pain relief, arthritis, arthrosis, tendinitis, tendinosis, apohysitis, myositis, myalgia, taut muscular bands, soft tissue inflammation and as synovial replacement composition for, for example, treating osteoarthritis.

The hydrogel may be formed in situ (in vivo) sub-cutaneously, intra-peritoneally, intra-muscularly or within biological connective tissues, bone defects, fractures, articular cavities, body conduits or cavities, eye cul-de-sac, or solid tumors.

The polysaccharide solution may be introduced within an animal or human body by injection or endoscopic administration.

Drugs, polypeptides, living microorganisms, animal or human cells may be incorporated within the polysaccharide solution prior to gelation.

In accordance with the present invention there is also provided the use of the polysaccharide gel formed from the compositions described herein for producing biocompatible degradable materials used in cosmetics, pharmacology, medicine and/or surgery.

Herein, a hydrogel is referred to a semi-solid gel formed from the chitosan aqueous solutions described herein, upon subjecting these solutions to the physiological conditions described herein. The hydrogel is preferably formed in vivo, upon administration of the chitosan composition, but can alternatively be formed ex-vivo prior to its utilization.

The gel may be incorporated as a whole, or as a component, into implantable devices or implants for repair, reconstruction and/or replacement of tissues and/or organs, either in animals or humans.

The gel may be used as a whole, or as a component of, implantable, transdermal or dermatological drug delivery systems.

The gel may be used as a whole, or as a component of, opthalmological implants or drug delivery systems.

The gel may be used for producing cells-loaded artificial matrices that are applied to the engineering and culture of bioengineered hybrid materials and tissue equivalents.

The loaded cells may be selected from the group consisting of chondrocytes (articular cartilage), fibrochondrocytes (meniscus), ligament fibroblasts (ligament), skin fibroblasts (skin), tenocytes (tendons), myofibroblasts (muscle), mesenchymal stem cells, keratinocytes (skin), and neurons, as well as adipocytes or bone marrow cells. In fact cells from any tissue which are capable of proliferation may optionally be embedded in such a construct.

A major detriment to wound heeling is the presence of biofilm. Biofilm is composed of at least 80 percent extracellular macromolecules that are usually positively charged, similar to chitosan. Chitosan may optionally be used as a biofilm disruptor thus helping wound hygiene and limiting the inhibitory effect of biofilm on destruction of bacteria. Chitosan gel mixed with lactoferrin may optionally act as a slow release reservoir to destroy biofilm in any chronic wound or a wound that may become chronic. Chitosan gel mixed with xylitol may optionally also be a specific biofilm disruptor.

In accordance with the present invention there is also provided the use of loaded polysaccharide gel as injectable or implantable gel biomaterials which act as supports, carriers, reconstructive devices or substitutes for the formation in situ of bone-like, fibrocartilage-like or cartilage-like tissues at a physiological location of an animal or a human.

For example, chitosan gels according to the present invention may be useful as a sustained delivery drug-system for treatment of the eye. Results based on the ocular irritation test of chitosan compounds have indicated that chitosan preparations are suitable for use as ophthalmic gels based on their excellent tolerance (Molinaro et. al., 2002).

In accordance with a further embodiment of the present invention, a slow release drug delivery hydrogel system is provided comprising highly acetylated type 1 chitosans and highly deacetylated type 2 chitosans.

Any of the drug delivery systems of the present invention may be used for delivery of a wide variety of drugs, including, but not limited to, analgesics, anesthetics, antiacne agents, antiaging agents, antibacterials, antibiotics, antiburn agents, antidepressants, antidermatitis agents, antiedemics, antihistamines, antihelminths, antihyperkeratolyte agents, antiinflammatory agents, antiirritants, antilipemics, antimicrobials, antimycotics, antioxidants, antipruritics, antipsoriatic agents, antirosacea agents antiseborrheic agents, antiseptics, antiswelling agents, antiviral agents, antiyeast agents, cardiovascular agents, chemotherapeutic agents, corticosteroids, fungicides, hormones, hydroxyacids, keratolytic agents, lactams, mitocides, non-steroidal anti-inflammatory agents, pediculicides, progestins, sanatives, scabicides, and vasodilators.

In some embodiments, the drug is an ACE inhibitor or an anti-inflammatory drug.

In accordance with a further embodiment of the present invention, A process for preparing a stable pH-dependent and temperature-dependent chitosan hydrogel composition comprised of at least one acetylated chitosan having a degree of acetylation of from about 30% to about 60%, and at least one deacetylated chitosan having a degree of deacetylation that is about 70% to about 95%, which process comprises:

a) dissolving said acetylated chitosan and said deacetylated chitosan in an acidic aqueous solution at a temperature between 0° C. to 10° C., to thereby form a composite solution, wherein the ratio of said acetylated chitosan and said deacetylated chitosan in said composite solution is in the range of 1:1 to 4:1;

b) adjusting the pH of said composite solution to a value of 6.6 to 7.4 at a temperature between 0° C. to 10° C.; and c) increasing at least one of the temperature of said composite solution to about 37° C. and/or raising the pH to physiological pH.

It is to be noted that the composite solution may present different pH values at different temperatures. In example, pH values at 4° C. correlate to pH values which are lower by about 0.5 units at 25° C. Thus, a composite solution at 4° C. with pH 7.4 may present about pH 6.9 at 25° C.

In some embodiments, dissolving of the highly acetylated chitosan and the highly deacetylated chitosan is performed simultaneously in the same vessel.

Optionally, dissolving the highly acetylated chitosan and the highly deacetylated chitosan is performed in separate vessels to form two solutions. In such embodiment, the process further comprises mixing these two solutions to form the composite solution.

Further according to some embodiments of the present invention there is provided a pH-dependant and temperature-dependant hydrogel formed by the process described herein.

The present inventors have further found that a mixture of a highly deacetylated chitosan and chitosan oligomers, also forms a hydrogel having the desired properties, as described hereinabove.

Thus, according to a further aspect of embodiments of the present invention, there is provided a chitosan composition, which forms a hydrogel at near physiological pH and 37° C. the composition comprising at least one type of a highly deacetylated chitosan having a molecular weight of from 10-4000 KDa (a chitosan polymer) and a degree of deacetylation of at least 70%, and at least one type of a chitosan having a molecular weight of from 200-20000 Da (namely, a chitosan oligomer), the composition being in a form of an aqueous solution.

The chitosan oligomer can be a highly deacetylated chitosan oligomer having a degree of deacetylation of at least 70% and/or a highly acetylated chitosan oligomer having a degree of acetylation of from 30% to 60%.

In some embodiments, the ratio between the highly deacetylated chitosan polymer and the chitosan oligomer is higher than 1:1, and can be in the range of from 2:1 to 20:1, depending, inter alia, on the MW of the highly acetylated chitosan and the chitosan oligomers.

Accordingly, the concentration of the highly acetylated chitosan polymer can be, for example, 1%, 2%, 4%, 10% and any concentration is the range of 1-20% (w/w).

The concentration of the chitosan oligomers is selected according to the desired ratio.

The chitosan oligomers are water-soluble at a pH of 6.5 and higher and thus can also serve as "protectors", as discussed herein.

Such hydrogels can be utilized in any of the applications described herein and are prepared as described in Example 8 hereinbelow.

As used herein the term "about" refers to ±10%.

As used herein, the term "pseudo-thermosetting" in connection with the composition of the present invention means that temperature does not induce the gelation of the composition but acts rather as a catalyst which dramatically shortens the gelation time when risen.

As used herein, the term "neutralized" means a pH of 6.8-7.2.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Example 1

Preparation of Chitosan Hydrogel

Chitosan with a degree of acetylation of 15% and molecular weight of 65 KDa (Koyo, Japan) was dissolved by mixing with 0.9% HCl for 24 hours, forming a type 1 chitosan solution having a chitosan concentration of 3% (w/v).

Homogenously deacetylated chitosan with 51% deacetylation and molecular weight of 220 KDa (Koyo, Japan) was dissolved by mixing with 0.9% HCl for 24 hours, forming a type 2 chitosan solution having a chitosan concentration of 3% (w/v).

The type 1 and type 2 chitosan solutions were mixed according to the following ratios of type-1 to type-2: 1:1, 1:2 and 1:3, titrated to pH 6.8 and left for 24 hours at 4° C., followed by further titration to pH 7.2 at 4° C. with sodium hydroxide.

The resulting composition was liquid at room temperature. Upon increasing the temperature to 37° C. and raising the pH to 7.4, the liquid solution formed a stable semi-solid gel, as illustrated in FIG. 1.

Example 2

Degradation Profiles of Chitosan Gels

Pseudo-thermosetting hydrogel (3% w/v) was prepared at a ratio of 1:1 w/w of homogenous (type 2) to non-homogenous chitosan (type 1), as described in Example 1 above.

One gram of the gel was placed in 50 ml plastic tubes, in triplicate.

Aliquots of 3 ml of 10% bovine serum media were added to each tube for predefined times intervals (1, 2, 3, 4, 5, 6, and 7 days). At the end of each time interval, the gel was washed 3 times over a period of 24 hours by repeatedly adding 50 ml of distilled water, leaving at room temperature for a few hours and removing the water. The washing process removed all soluble materials from the gel.

The gel was then frozen, lyophilized and weighed. Weight degradation was calculated from the change in weight of the samples, as a function of time interval.

Figure 2A:
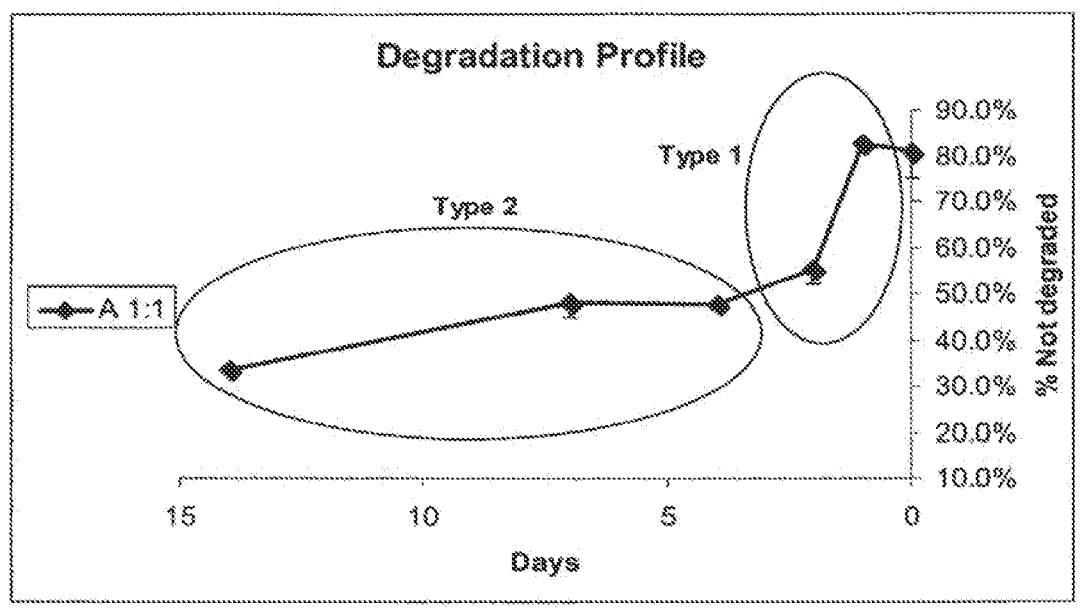
FIG. 2a illustrates degradation times of a hydrogel composition comprising chitosan type 1 and type 2 in accordance with some embodiments of the present invention.
Figure 2B:
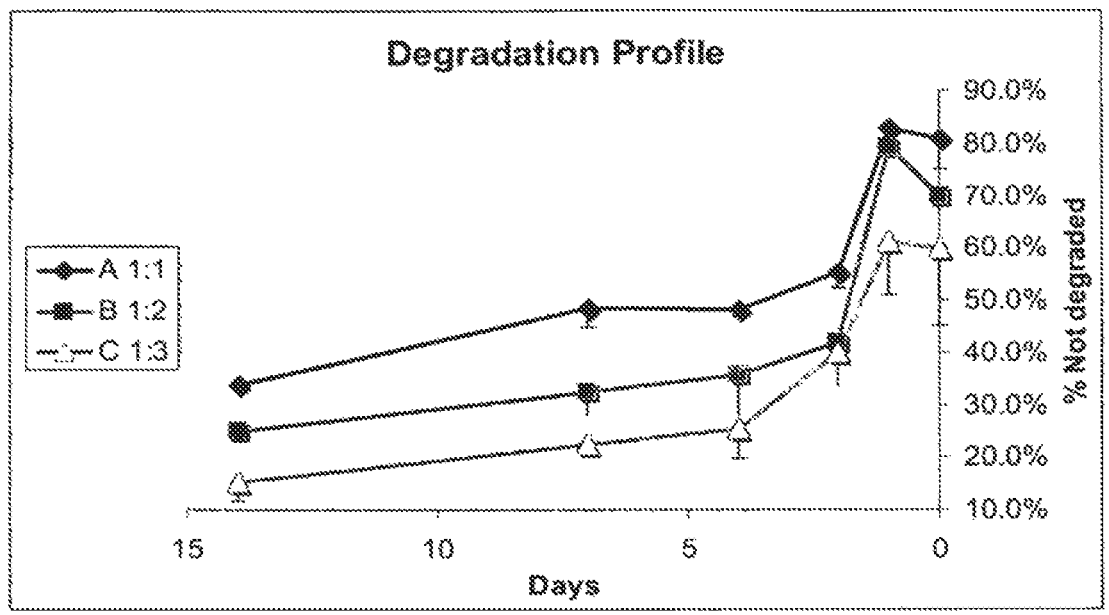
FIG. 2b illustrates degradation times of a hydrogel composition comprising chitosan type 1 and type 2 at different ratios.

The degradation of the hydrogel by serum enzymes is shown in FIGS. 2a and 2b.

Two distinct types of degradation kinetics are shown in FIG. 2a, a fast phase that terminates within 3-6 days and a slower one that exhibits only partial degradation after 14 days. It is believed that the fast phase reflects degradation of type 2 chitosan, which is highly soluble and readily recognized by serum enzymes. The slow kinetic phase is related to chitosan type 1 chitosan, which is not readily recognized and digested by serum enzymes.

Controlling the reacetylation of glucosamine polymer is a very important tool for manipulating the extent of recognition of the chitosan by lysozyme and consequently for manipulating the rate of hydrogel degradation. The main factor that controls the activity of the enzyme is the percentage of N-acetyl glucosamine (NAG) in the polymer (Ran et al., 2005). For this reason decreasing the reacetylation degree from 50% to 35% in chitosan Type 2 should allow the rate of degradation to be significantly decreased, resulting in a much shallower slope. On the other hand, increasing the degree of acetylation of chitosan Type 1 should result in faster degradation of the polymer. Selection of the appropriate combination of the two types of chitosans is expected to result in a single, linear degradation curve over time, instead of the two slopes shown in this Figure.

Reference is now made to FIG. 2b that illustrates mixtures of type 1 and type 2 chitosans in ratios of type 1 to type 2 of 1:1, 1:2 and 1:3. As shown in FIG. 2b, the rate of degradation of the gel is increased with increasing ratios of type 2 chitosan to type 1.

Example 3

Slow Release of Proteins by Chitosan Gels

In order to study the potential of the chitosan pseudo thermosetting hydrogel presented herein as a slow release vehicle, hemoglobin and bovine serum albumin (BSA) were used as solutes. These compounds are well accepted as protein standards.

To one ml solution containing a chitosan mixture as described in Example 1 above, in which the final concentration of both chitosans is 3.5%, a 25 µl aliquot of BSA or 40 µl of hemoglobin were added, resulting in a final concentration of 1 mg/ml and 4 mg/ml protein in the hydrogel, respectively. The protein-containing hydrogels were incubated in 3 ml PBS for one week at 37° C. The media was replaced daily, and the amounts of the released protein from the hydrogel was measured, as shown in FIGS. 3-7.

Figure 3:
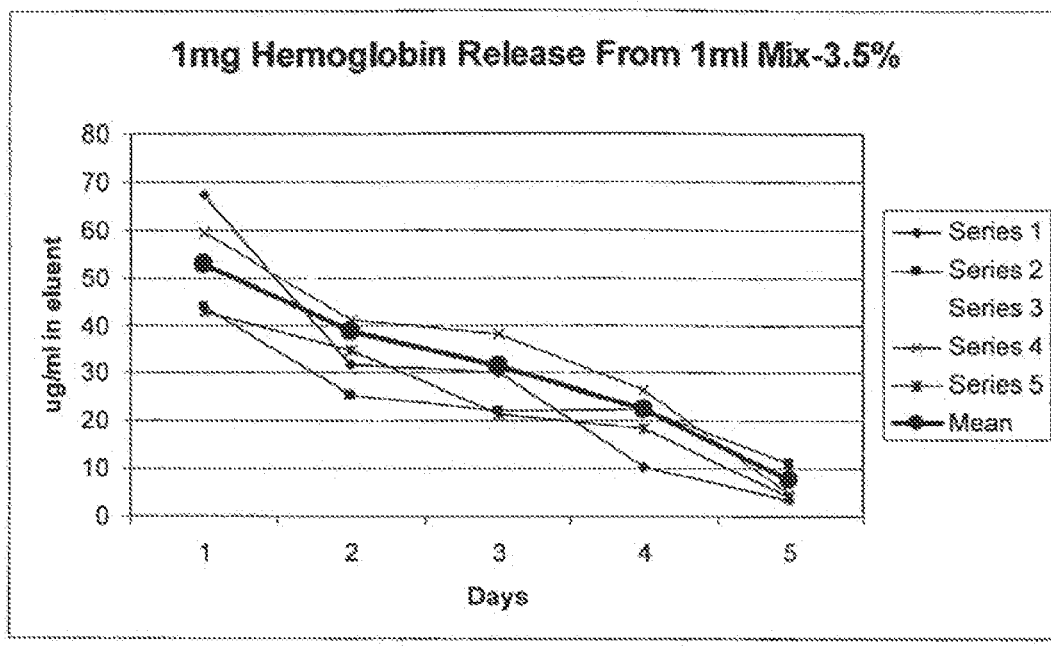
FIG. 3 illustrates release of hemoglobin from a hydrogel composition according to some embodiments of the present invention, as measured by µg/ml in eluent.

As shown in FIG. 3, in all the tested series, high amounts of hemoglobin were initially released and the rate of release decreased with time. No initial burst was shown.

Figure 4:
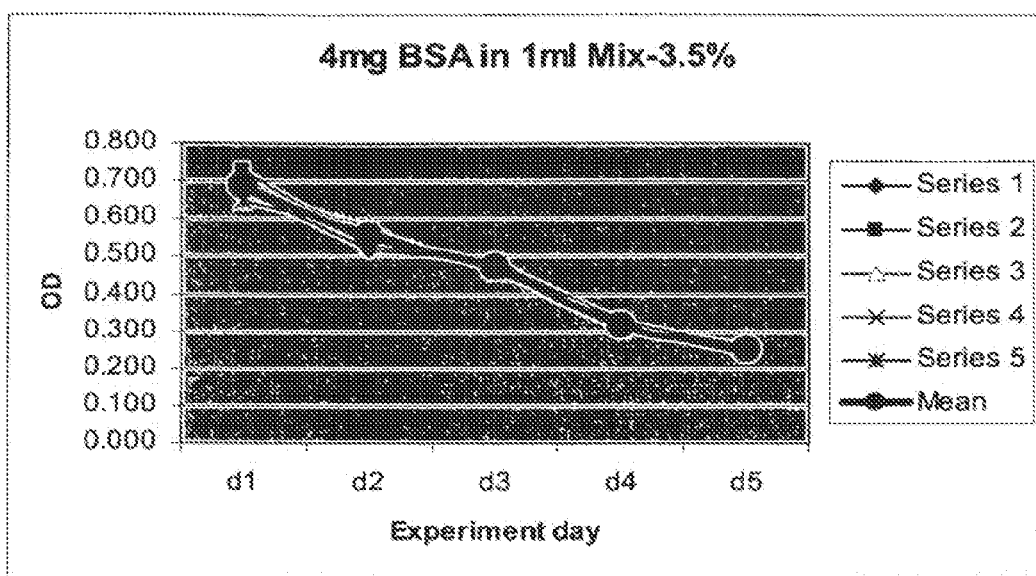
FIG. 4 illustrates release of bovine serum albumin (BSA) from a hydrogel composition according to some embodiments of the present invention as measured by optical density (OD)
Figure 5:
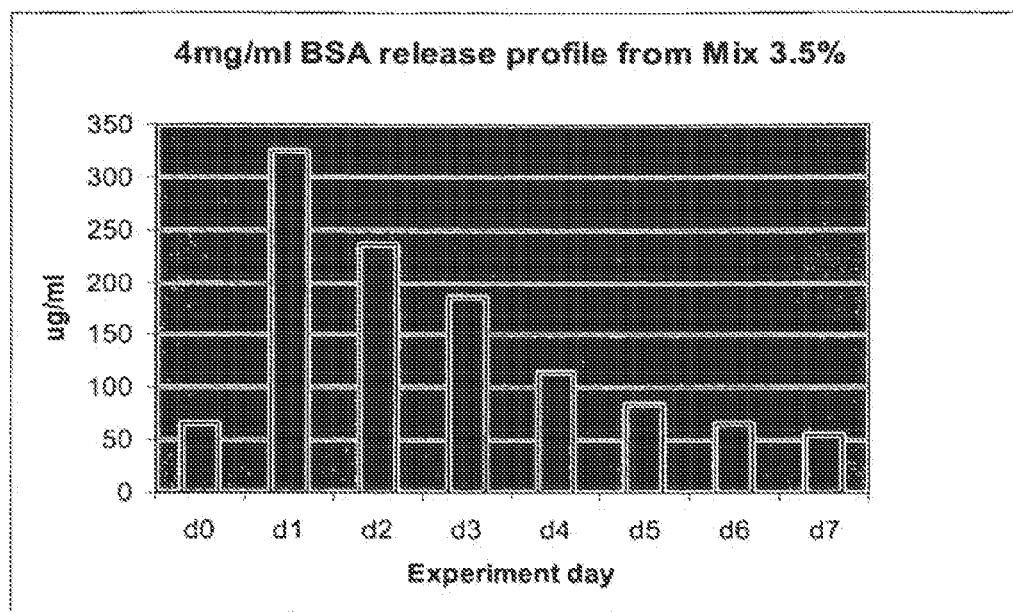
FIG. 5 presents a bar chart illustrating release of BSA from a hydrogel composition according to some embodiments of the present invention.
Figure 6:
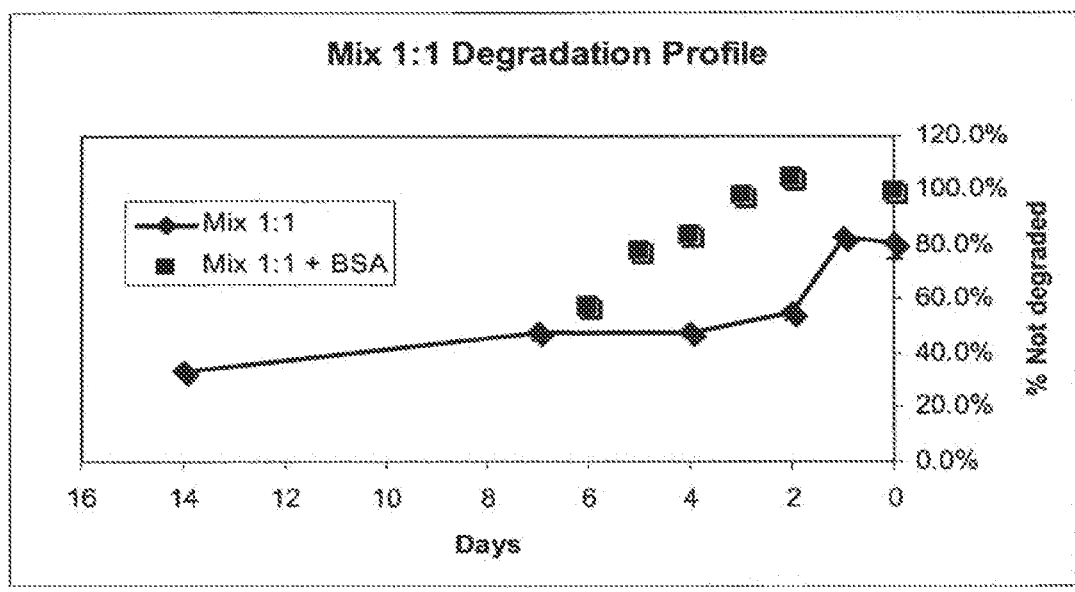
FIG. 6 illustrates the degradation profile of a hydrogel composition according to some embodiments of the present invention.

BSA showed the same profile as hemoglobin (FIGS. 4 and 5). A near linear slope was obtained (FIG. 4). Mixing of the BSA with the gel improved the gel's stability, providing a decreased degradation rate compared to that of the chitosan mixture alone (FIG. 6).

Comparison of the amounts of the released BSA versus the amounts of the degraded gel (FIG. 7) showed that the rate of release of the protein was faster than the rate of gel degradation.

Figure 7:
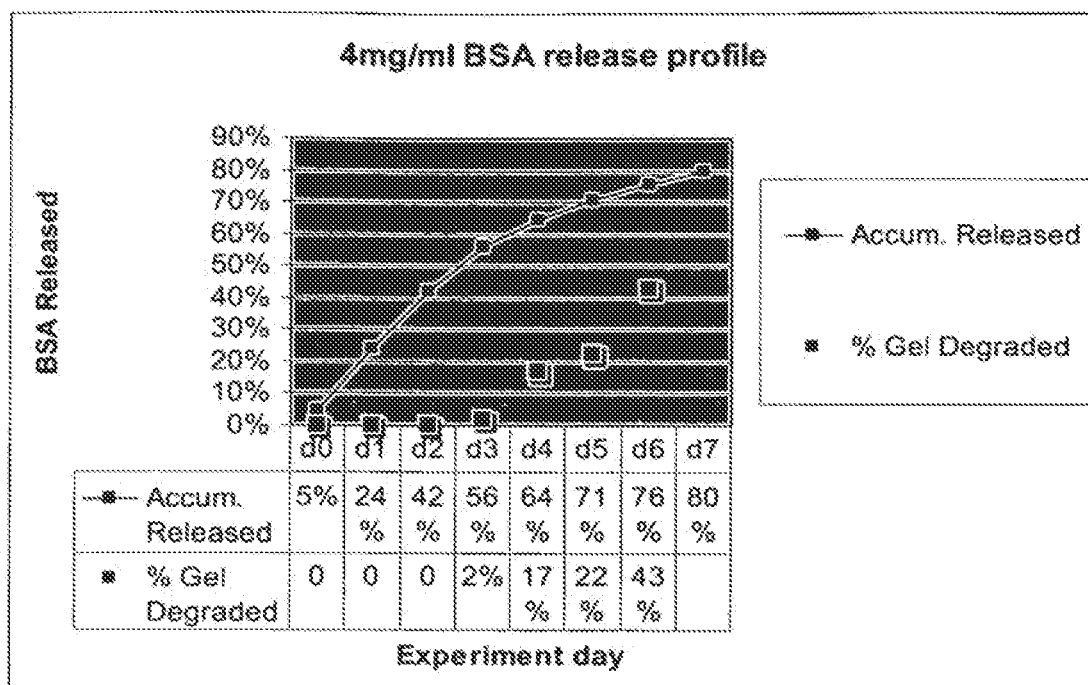
FIG. 7 illustrates the integration of the release profile of BSA with the degradation profile of a hydrogel composition according to some embodiments of the present invention.

The data shown in FIG. 7 relate to a single degree of acetylation of type 1 chitosan and a single molecular weight, which resulted in a protein release profile having a rate of release which decreased each day. However, appropriate selection of additional variables such as degree of reacetylation and molecular weights of the two types of chitosans allows the characteristics of the gel to be determined, and enables affinity of the protein drug for the chitosan structure to be improved. Such specific combinations would be expected to provide a fixed rate of release of a specific drug, reflecting a combined diffusion and matrix degradation rate.

Example 4

In vivo Study of Chitosan Gel as Wound Dressing

Psammomys obesus strain rats, which are known to develop diabetic symptoms when raised in captivity on a high fat diet, were used as a model of type II Diabetes mellitus. These animals are considered to be an excellent model for simulating chronic skin ulcers of diabetics, and study of skin wound healing, due to their tendency to develop profound infections, gangrene and sepsis, leading to morbidity and even mortality.

The following are the common parameters for examining skin ulcers healing:
1. Timing of neovascularization appearance in the reparative tissue.
2. Reduction in neutrophil activity.
3. Accelerated macrophage activity.
4. Timing of scar wound closure by a complete re-epithelialization of the wound.
5. Formation of keratinocytes monolayers.
6. Binding of the epidermis and the dermis layers by activation of the fibroblast-depositing extracellular matrix network.

A chitosan-based gel, serving as a biological dressing, was used, avoiding the need for bandaging or suturing, and providing direct coating of the wound bed for enhanced healing. The rate at which various healing stages occurred, especially the wound contraction-scar shrinkage and closure stage, was studied over a period of eight days.

The composition of the chitosan mixture includes: FM80 (660 kDa, referred to in Example 7 hereinbelow), DAC-50 (220 kDa, referred to in Example 7 hereinbelow) and a mixture of acetylglucosamine oligomers from 1-7 units (Koyo, Osaka, Japan). The formulation includes the three components in a ratio of 1:0.8:0.2, respectively.

Twenty five female Psammomys obesus rats of mature age, each weighing 150-160 grams, were used.

Thirteen animals were found to have developed diabetes following administration of a high fat diet, starting from 4 to 6 weeks prior to day zero.

Six animals having normal euglycemia (normoglycemia), indicating resistance to development of diabetes upon feeding with a high fat diet, were used as a first control, and six animals with normoglycemia when fed on a normal low fat, low energy diet, were used as a second control.

At day zero, a round full depth punch biopsy of 6 mm diameter was made through the epidermis, dermis and hypodermis to the muscles, at the shaved skin of the neck, using a Metricoconverter-production device.

The injuries of seven diabetic animals were treated by administration of the chitosan based-gel of Example 1 to the wound area, while a further six animals were left untreated. The gel was reapplied to the wound area of the treatment group every day.

For a period of seven days all the animals were macro-photographed, and the dimensions of the wound measured every 3 days. Weight and blood glucose levels were measured once a week, using digital glucometer, (Ascensia Elite of Bayer), by absorbing a blood drop from a cut created at the tail of the rat.

After 7 days, the animals were sacrificed and full depth biopsies were performed. The skin was collected and placed in fixation solution. Skin samples were further processed for histological and immuno-histochemical staining procedures, to evaluate the differences between treated and untreated wounds.

Figure 8A:
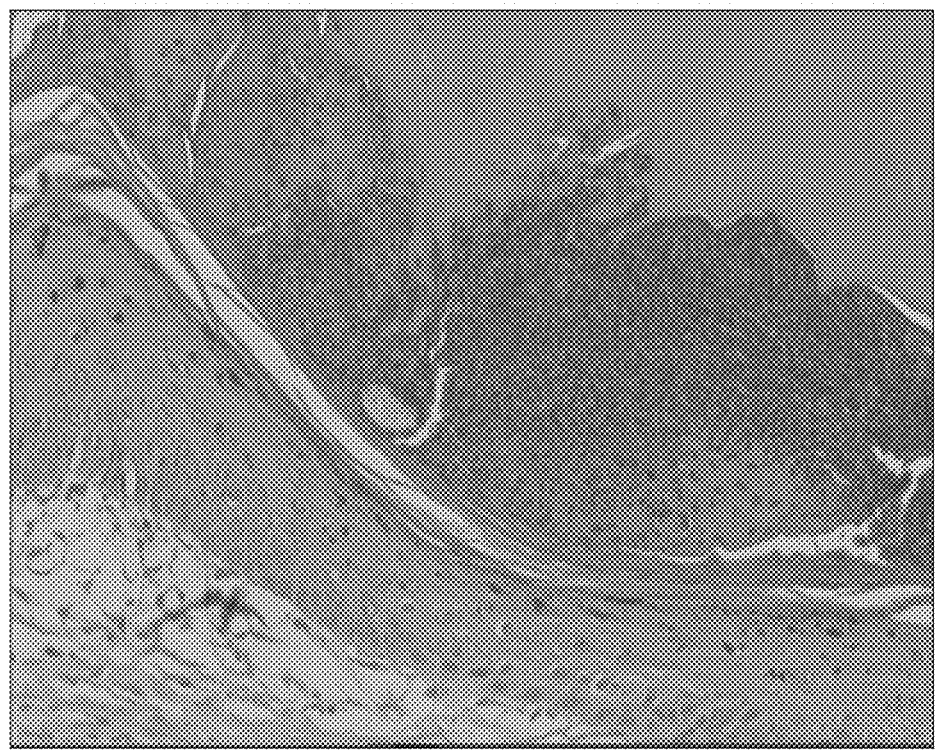
FIGS. 8A and 8B show histopathology of wound bed biopsies taken from rats treated with a hydrogel composition according to some embodiments of the present invention.
Figure 8B:
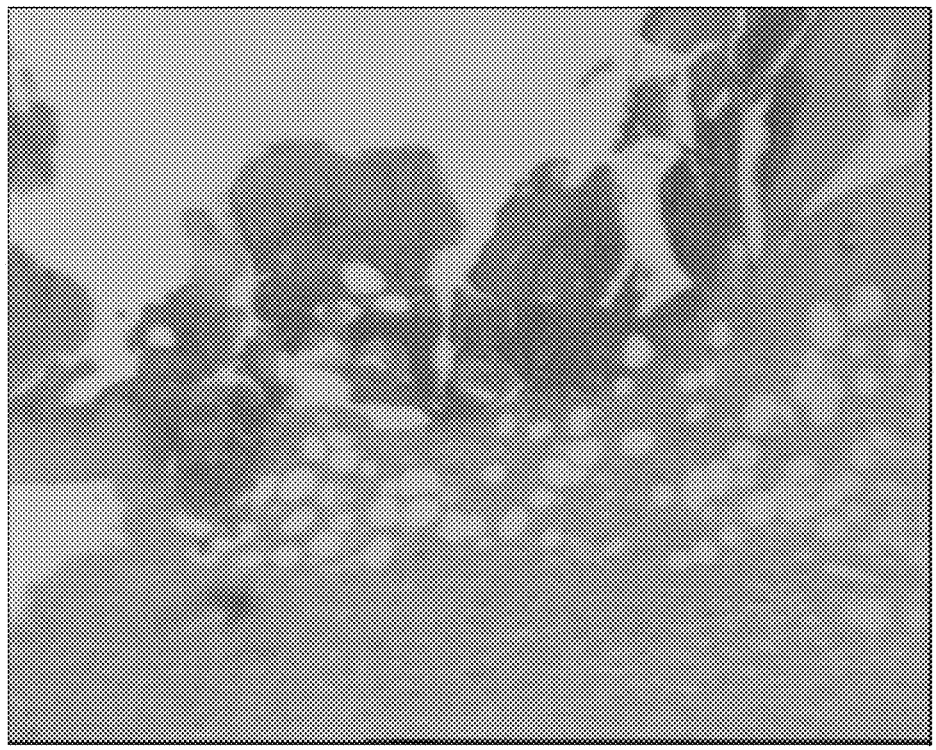
Figure 9:
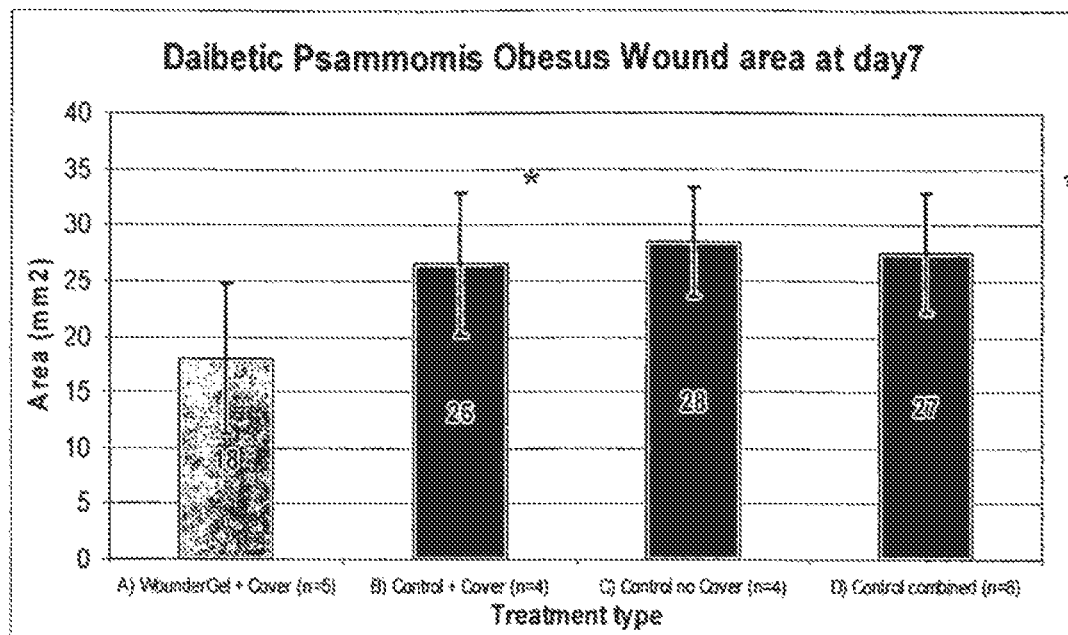
FIG. 9 shows a graph of the results of treating wound bed biopsies with a hydrogel composition according to some embodiments of the present invention.

Results are shown in FIGS. 8a and 8b and FIG. 9. As shown in these Figures, the treatment group showed a statistically significant increase in wound healing, and a reduction of the period of time required for wound healing, compared to the control group.

Example 5

Rotator Cuff Repair

Rotator cuff tears are a common source of shoulder pain. The incidence of rotator cuff damage increases with age and is most frequently caused by degeneration of the tendon, rather than injury from sports or trauma. Treatment recommendations vary from rehabilitation to surgical repair of the torn tendon(s). The best method of treatment is different for every patient and indeed many patients do not achieve satisfactory repair of their injuries.

The present invention, in some embodiments, overcomes these drawbacks of the background art by providing an injectable product allowing delivery of autologous cells into rotator-cuff tears under ultrasonographic control. In other embodiments, the injectable product allows the incorporation of bone-marrow cells as well, for example for tissue healing.

Preferably, the procedure is performed as an outpatient procedure or an ambulatory procedure requiring local anesthesia.

The initial liquid property of the gel allows full adherence to the tendon tear area.

In vivo experiments were performed on rats for tendon damage and repair (using surgically damaged tendons). The damaged tendons were sutured and were treated with a chitosan hydrogel as presented herein with bone marrow cells; the control animals only received sutures. 20 animals were studied for 3 months. Histologically proven tendon repair and prevention of muscle atrophy were both achieved (results not shown).

Figure 10A:
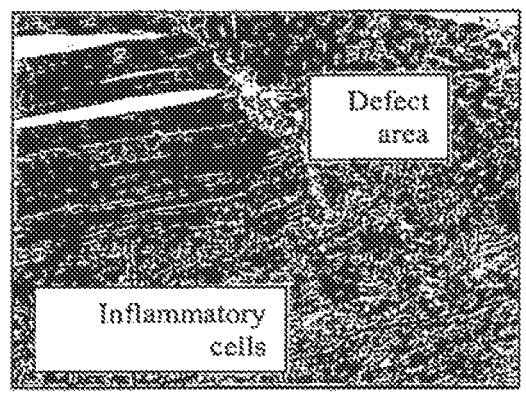
FIGS. 10A and 10B show the results of in vivo experiments performed on rats for rotator cuff damage.
Figure 10B:
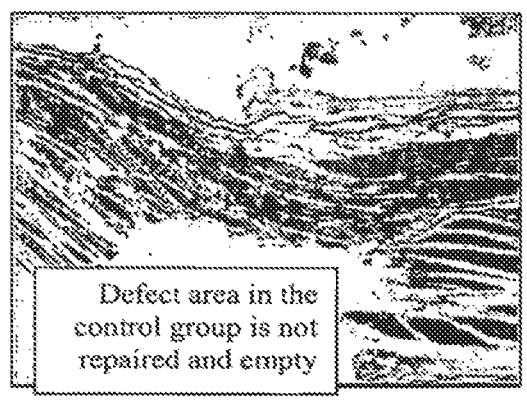

Also, in vivo experiments were performed on rats for rotator cuff damage, again surgically induced. This damage was treated as above. Histological slices of tissue, 6 weeks post surgery, show that endogenous cells were trapped from the neighboring tissues, improving the status of the injured site, compared to non treated control defects in the contra lateral shoulder. Exemplary results are shown in FIG. 10A (treated) and FIG. 10B (non-treated).

Example 6

A chitosan mixture is designed so as to serve as a reservoir of negatively charged substances such as proteoglycans (e.g., chondroitin sulfate), hyaluronate, and/or phospholipids (e.g., phosphatidyl choline). This unique mixture has special rheological properties simulating normal synovial fluid, allowing for cartilage regeneration and correction of joint mechanics.

In some embodiments, such a mixture comprises chitosan type 1 and chitosan type 2, as described herein, and further comprises one or more negatively charged substances, as described herein. In one example, the mixture comprises, in addition to the chitosans, phosphatidyl choline and chondroitin sulfate. In another example, the same mixture is utilized, while further comprising hyaluronate. The latter features a unique mixture of positively and negatively charged polymers, which provides to even improved rhelolgical and biological properties of the mixture.

A phospholipid-containing chitosan mixture, upon administration, forms a hydrogel composition which can serve as a synovial replacement, for use in, for example, treatment of osteoarthritis.

In order to evaluate the properties of these compositions, the static coefficient of friction was measured between 2 cartilage surfaces treated with hyaluronic acid (1%), a chitosan composition comprising 1% chitosan type 1 (having a MW of 660 KDa), 1% of a chitosan type 2 (having a MW of 220 KDa) (denoted as chi2gel), and a saline-treated system as a control, as described in http://www.pa.uky.edu/~phy211/Friction_book.html.

Figure 11:
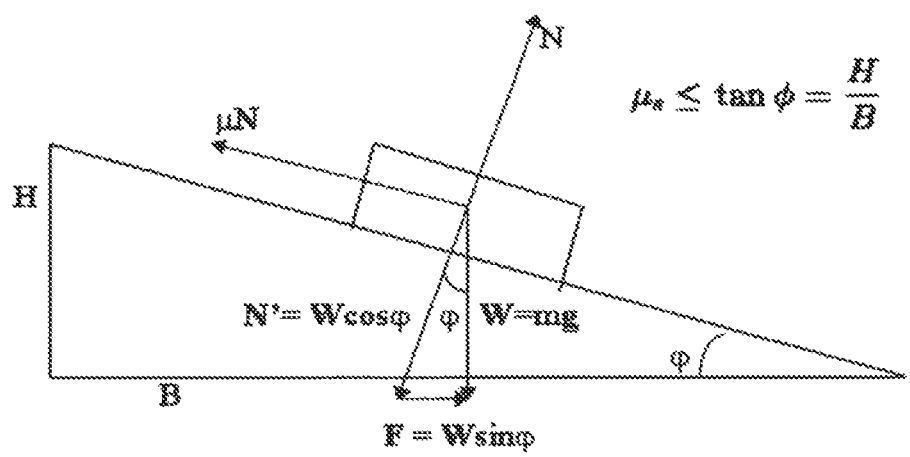
FIG. 11 presents a schematic illustration of measuring a friction coefficient.

FIG. 11 illustrates the model for measuring the static coefficient.

Figure 12:
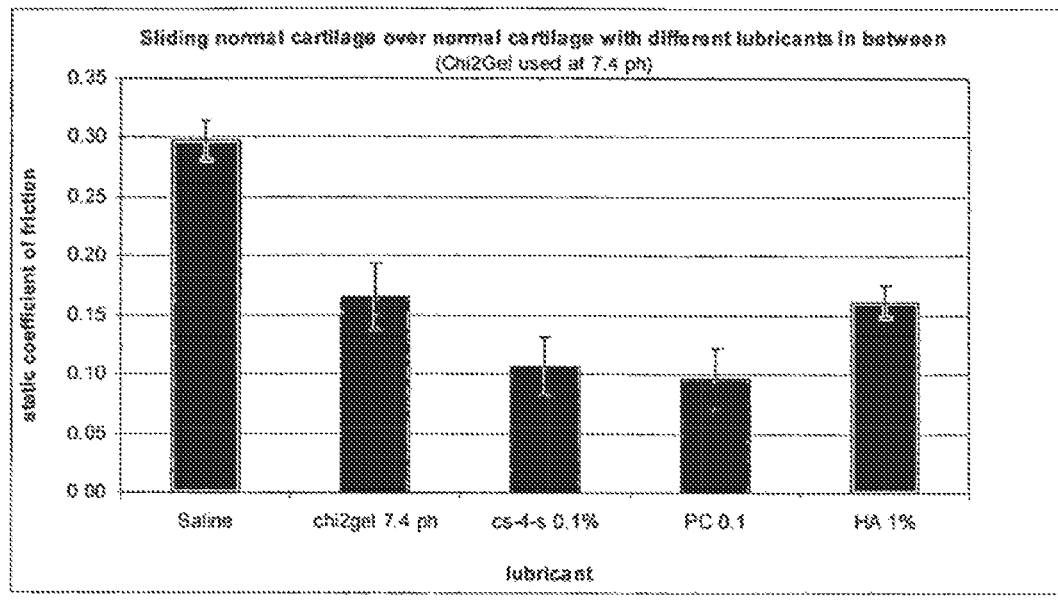
FIG. 12 show the static friction coefficient of hydrogel compositions according to some embodiments of the present invention, compared to a hyaluronic acid composition.

FIG. 12 presents the static friction coefficient between 2 layers of normal cartilage, as measured for: no gel (denoted as "saline"); a chi2gel as described hereinabove, a chi2gel comprising 0.1% Chondroitin Sulfate (denoted cs-4-s), a chi2gel comprising 0.1% Chondroitin Sulfate and 0.1% Phosphatidyl choline (denoted PC 0.1), and a Hyaluronic acid 1% solution (denoted HA 1%).

The obtained data clearly show that combining Chi2Gel with Chondroitin Sulfate and Phosphatidyl choline results in a synovial-like friction coefficient.

Example 7

Controlling the Conditions for Formation of a Chitosan Hydrogel

A chitosan polymer (or oligomer) is defined by its molecular weight, its degree of deacetylation, its crystallinity and the mode of distribution of its acetyl groups.

The solubility of chitosan in aqueous solutions is limited. For example, using HCl 0.15N, a chitosan having a MW above 200 KDa is dissolvable at concentrations lower than 10% (w/v) (higher MW means reduced maximal solution concentration). HCl 0.15N is a concentration which when fully titrated becomes the physiological NaCl concentration. Using higher concentrations of HCl (or other acid like acetic acid) allows higher concentrations.

The most common commercially available chitosan has a low DA (degree of acetylation) in the range of 5-30%, and is referred to herein as Chit-20. Such a chitosan is a type-1 chitosan, and it precipitates from a solution when at a pH above 6.5. Chit-20 solutions at physiological environments therefore do not exist, and most of the currently practiced applications involving implementation of chitosan utilize various types of solid chitosan (e.g. Procon's gasse).

A unique type of chitosan is a chitosan homogenously deacetylated to 50% or homogenously reacetylated to 30-60% (type 2 chitosan). Such a chitosan has a superior solubility in aqueous solutions, as compared to highly deacetylated chitosans (type 1) and typically remains soluble at neutral and physiological pH, depending on its concentration. An exemplary such chitosan, having a MW of 220 KDa is referred to herein as Chit-50. This type of chitosan, at a concentration of 3% (w/v) or more, forms a gel at pH higher than 7.5.

Gel Formation Using a Mixture of Chitosan Polymers:

When mixing chitosan type 1 (e.g., chit-20) and chitosan type 2 (e.g., chit-50) at a physiological pH and under certain conditions, no precipitation of the polymers is observed and instead, the mixture forms a gel. Gel formation involves "coating" (or "protection") of the chit-20 by the chit-50, and is effected by the affinity between the two chitosan types, which leads to interactions therebetween (e.g., hydrogen bonds, hydrophobic interactions and/or Van der Waals interactions).

The gelation process may be as short as several minutes or as long as many days and is demonstrated by a gradual yet continuous increase in the viscosity of the system.

In the conducted (ex-vivo) experiments, gel formation is defined by turning a glass tube that contains the initial solution on its side and determining whether the solution flows (or not) and remains stuck to the bottom of the glass tube. Gel formation depends on the type, shape and parameters (e.g., diameter) of tube, as well as the assay time frame.

In this study, gel formation was defined as follows: a one ml solution was placed in a 14 mm (in diameter) round-bottomed glass tube and was incubated at 37° C. overnight. Thereafter, the glass tube was turned into a horizontal position and the presence or absence of liquid flow was determined. Absence of liquid flow indicated that a gel was formed. The gel contains the whole amount of water and remained rigid in a semi solid state. Presence of flow but in a "well distinguished" structure also indicated that a gel was formed. The presence of liquid flow and/or the formation of two separate phases, solid and liquid, indicated that a gel was not formed.

Controlling Gel Formation:

Materials:

Two commercially available highly deacetylated chitosan polymers (chitosan type 1) were used in this study:

FM80 (MW=660 kDa; 85% DDA (degree of deacetylation); and

FM80S (MW=420 kDa; 91.3% DDA), both obtained from Koyo, Osaka, Japan.

As a highly acetylated chitosan (chitosan type 2), DAC50 (MW=220 kDa; 50% DDA), also obtained from Koyo, Osaka, Japan, was used.

Assay Protocol:

Preparation of Stock Solutions: A chitosan polymer (as a powder) was mixed with HCl 0.15N and the solution was agitated during 24 hours at room temperature.

The following stock solutions were made:

| FM80-2 | (2% (w/v) solution of 660 kDa Chit-20) |
| FM80S-2 | (2% (w/v) 420 kDa Chit-20) |
| DAC50-3 | (3% (w/v) 220 kDa Chit-50). |

Mixture Formation: the above-described stock solutions, mixtures having a defined final concentration (w/v) of each chitosan and a defined ratio thereof, were prepared. An exemplary mixture is FM80:DAC50 1.2:1.2, in which each of the chitosans are at a final concentrations of 1.2% (w/v), and the ratio therebetween is 1:1.

Titration: The above-described mixtures were slowly titrated, while being cooled in ice water (0° C.), with NaOH (at 2N, 1N and 0.5N concentrations), until a pH of about 7.3 was achieved. One ml samples were then continuously taken from the mixture during the titration and each sample was placed in a 14 mm glass tube. The samples were sealed and placed in an incubator at 37° C. overnight.

Gel Formation Testing: Each glass tube was placed in a horizontal position and gel formation was determined as described hereinabove.

Results:

Table 1 below presents the results obtained for various FM80:DAC50 mixtures:

TABLE 1

| Mixture | | | Mix Ratio | | | | |
|---|---|---|---|---|---|---|---|
| FM80-2 | 50-3 | HCl•15N | FM80:DAC50 | Gel Formation at various pH values* | | | |
| 3 | 2 | 0 | 1.2:1.2 | 7.32 | 7.42 | 7.5 | 7.66 |
| | | | | N | Y | Y | Y |
| 2.5 | 1.667 | 0.833 | 1:1 | 7.35 | 7.43 | 7.6 | 7.7 |
| | | | | N | N | Y | Y |
| 2 | 1.333 | 1.667 | 0.8:0.8 | 7.27 | 7.4 | 7.48 | 7.54 | 7.62 |
| | | | | N | N | N | N | N |
| 1.5 | 1 | 2.5 | 0.6:0.6 | 7.32 | 7.43 | 7.52 | 7.6 |
| | | | | N | N | N | N |
| 2.5 | 1 | 1.5 | 1:0.6 | 7.4 | 7.47 | 7.54 | 7.61 |
| | | | | N | N | N | N |

*Y = yes, a gel is formed; N = no gel formed

The results show that a mixture of a 660 kDa chitosan type 1, with AD of 15% (and similar crystallinity as in FM80) and DAC50 at equal (1:1) w/w ratios forms gel at near pH=7.5, when a final concentration of each chitosan is higher than 0.8% (w/v).

Such a mixture, at final concentrations of 1.2% (w/v) of each chitosan, forms a gel at a wider pH range (below 7.42), as compared to a mixture at a final concentration of 1% (w/v) of each chitosan (above 7.43), thus indicating that at higher final concentrations the pH range for gel formation is increased (as discussed hereinbelow).

At a FM80:DAC50 ratio higher than 1:1 (e.g., 1:0.6), no gel is formed.

Table 2 below presents the results obtained for various FM80S:DAC50 mixtures:

TABLE 2

| Mix formula | | | Mix Ratio | | | | | |
|---|---|---|---|---|---|---|---|---|
| FM80S-2 | 50-3 | HCl•15N | FM80S:DAC50 | Gel Formation at various pH values* | | | | |
| 3 | 2 | 0 | 1.2:1.2 | 7.37 N | 7.40 Y | 7.44 Y | 7.50 Y | |
| 2.5 | 1.667 | 0.833 | 1:1 | | 7.44 N | 7.53 Y | 7.63 Y | |
| 9 | 1.333 | 1.667 | 0.8:0.8 | | 7.42 N | 7.51 N | 7.61 N | 7.7 N |
| 1.5 | 1 | 2.5 | 0.6:0.6 | | 7.44 N | 7.55 N | 7.63 N | |

*Y = yes, a gel is formed; N = no gel formed

These results further support the findings that a minimal concentration of each polymer is required in order to achieve gel formation at near pH=7.5 at the indicated conditions.

This study has shown that parameters influencing gel formation in the tested systems include pH, the relative ratio (w/w) of the chitosan type-1 and type-2 polymers, the molecular weight (MW) of each chitosan polymer, the final concentration of each chitosan polymer and the temperature, as follows.

pH: gel formation is pH-dependent, such that solution mixtures form a gel only within a certain range of pH. This pH range is increased as the final concentrations of the chitosans are increased. The absolute pH values increase as the final concentrations of the chitosans decrease.

For example, for a chitosan type 1 (chit-20) having MW of 420 kDa and a chitosan type 2 (chit-50) having MW of 220 kDa, each at a concentration of 1%-1.2% and at a 1:1 w/w ratio, the pH range in which a gel is formed at 4° C. is 7.4-7.7. At higher pH values, precipitation is observed.

It is noted that pH values at 4° C. correlate to pH values lower by 0.5 units at 25° C. Thus, pH 7.4 at 4° C. is found to be pH 6.9 at 25° C.

Final Concentration of Chitosan Type 1 (e.g., Chit-20): The chitosan type 1 is the backbone of the formed gel. Hence, gel formation depends on the final concentration of this type of chitosan. It is assumed that as the MW of the chitosan type 1 increases, the final concentration decreases, and vise versa, as the MW decreases the final concentration increases.

Molecular Weight of Chitosan Type 1 (e.g., Chit-20): It is assumed that at higher MW of the highly deacetylated chitosan (type 1), the pH working range (the range that allows gel formation) decreases, for example, from 7.4-7.7 for 660 kDa chitosan to 7.0-7.3 for 2,000 kDa chitosan. It is further assumed that at higher MW the relative concentration of the type 2 chitosan (e.g., Chit-50) required is increased. It is further assumed that the concentration of type 1 chitosan (e.g., chit-20) decreases (e.g., to 0.5%), whereby the pH values required for gel formation would shift to 7.2-7.4 (at 4° C.).

It is further assumed that as the molecular weight (MW) chitosan type 1 or 2 decreases (e.g., from 420 kDa to 200 kDa), the concentration of this chitosan required to form a gel increases. Exemplary such concentration is 1.5% (w/v) and higher (with a similar concentration of the type 2 chitosan). pH values for gel formation in such conditions are expected to shift to 7.5-7.8 (at 4° C.).

Concentration of Chitosan Type 2 (e.g., Chit-50): A minimal relative concentration of Chit-50 is required for gel formation (e.g., a 1:1 ratio). In addition, keeping Chit-20 at constant final concentration and increasing the concentration of Chit-50 extends the range of other parameters for gel formation (for example, increases the pH working range). Increasing the concentration of Chit-50 further decreases the pH at which a gel is formed.

Molecular Weight of Chitosan Type 2 (e.g., Chit-50): It is expected that using Chit-50 having a MW higher than 220 kDa will enable to use a reduced relative concentration of Chit-50 in the mixture. Higher MW of chitosan type 2 results in high protection and improved stability of the chitosan type 1 (having any MW). At such conditions, the pH range for gel formation is expected to increase.

For example, for a 2000 kDa chitosan type 2 with a 660 kDa chitosan type 1, pH for gel formation should be about 7.8, and for a 2000 kDa chitosan type 2 and a 2000 kDa chitosan type 1, pH for gel formation should be about 7.6.

Temperature: The temperature appears to affect the rate of gel formation linearly. Thus, at 37° C., the gel will form faster than at room temperature or at 4° C.

Relative Ratio of Chitosan Type 1 and Type 2: The ratio required for gel formation depends on the MW of each chitosan. For example, as the MW of type 1 chitosan increases (e.g., to 2000 kDa), its required concentration can be reduced possibly to about 0.5%. However, it is assumed that the ratio between type 2 and type 1 would increase to, for example, (2:1), 3:1 and even 4:1.

Increasing the MW of type 2 chitosan from 220 kDa to e.g., 2000 kDa, the minimal concentration thereof required for gel formation decreases to e.g., 0.5% (instead of 1%), such that when high MW type 1 chitosan is used, the ratio would be about 1:1.

Example 8

Chitosan Hydrogels Formed from Highly Acetylated and Highly Deacetylated Chitosan Oligomers and a Highly Deacetylated Chitosan Polymer Oligomers of highly deacetylated chitosan (e.g., chit-20) do not precipitate at pH higher than 6.5, as opposed to similar polymers. Thus the formation of a gel from a mixture of highly deacetylated chitosan oligomers (e.g., MW of 200-20000 Da) and highly deacetylated chitosan polymers (e.g., MW of 200-2000 KDa) was tested.

Solutions of chit-20 polymers as described in Example 6 hereinabove were each mixed with a solution of a chit-20 oligomer (MW=200-1500 Da), the latter serving in a similar role of "coating" much as chitosan type 2, for protecting the type I chitosan polymer from precipitation. The tested final concentration of the chit-20 oligomers was 1%, 2%, 4% and 10% and the final concentration of the high MW chit-20 polymer (e.g., FM80) was 1%. The tested ratios (oligomer to polymer) were 1:1; 2:1; 4:1; and 10:1.

Except at a 1:1 ratio, all tested mixtures formed a chitosan hydrogel, surprisingly indicating that oligomers of highly deacetylated chitosan (e.g., chit-20) can also provide the required protection for obtaining the desired hydrogel.

Gel formation was also observed with FM80s (MW of 420 kDa) and highly deacetylated chitosan oligomers having MW of (MW=200-2000 Da), at a ratio of 1:3.

Similar results, namely gel formation, are obtained for mixtures of highly deacetylated chitosan polymers (e.g., MW of 200-2000 KDa) and highly acetylated chitosan oligomers (e.g., chit-50 oligomers having MW of 1000-20000 Da).

Example 9

Intraarticular Injection of a Chitosan Composition Comprising Hyaluronate Delays Osteoarthritis Progression and Reduces Pain in a Rat Meniscectomy Model Animal Models and Procedures.

Wistar rats of 0.3-kilogram-weight male rats were used in the study. Knee osteoarthritis occurs predictably after partial medial meniscectomy. The disease develops in a time-dependent and predictable fashion. It is a common model assessing the effect of antiosteoarthritis drugs. General anesthesia was induced by Ketamine 80 mg/kg and Xylazine 8 mg/kg. In the right knee, 200-microliters of 2% (w/v) chitosan-hyaluronate hybrid gel was injected at the time of meniscectomy in 9 animals and two week after meniscectomy in another four animals. The contralateral knee served as control to either saline or hyaluronate (1% gel 200-microliters, produced by Savient Pharmaceuticals, Inc., East Brunswick, N.J., USA) injection. The rats were allowed unrestricted motion after the surgery and evaluated every six weeks under image intensification. The following parameters were evaluated: degree of medial joint space opening and unloaded joint space width. After 3 months, the animals were sacrificed, and histological examination was performed. Animal knees were randomized after incapacitance testing demonstrated similar weight-bearing on both hindlimbs. In one knee, either saline (in 4 animals) or hyaluronate was injected (5 animals). In the contralateral knee, chitosan-hyaluronate mixture was injected. In another four animals, the injection was performed under general anesthesia one week after meniscectomy.

Chitosan-Hyaluronate Hybrid Gel.

A chitosan hyaluronic acid hybrid has been used. Briefly, a mixture of chitosans and oligochitin (FM80, DAC50, and oligochitin from Koyo chemicals Ltd., Japan) was solubilized in HCl 0.13N and titrated with sodium hydroxide to pH of between 6.6 to 7.2. This was followed by an addition of hyaluronic acid (molecular weight of 3 million Dalton, Ferring Ltd.). Genepin (Challenge Bioproducts Co., Ltd., Taiwan), a natural cross-linker is added to the chitosan hyaluronic acid composition at 0.2% (w/v) just before injecting in order to accelerate the gelation.

Incapacitance Tester Evaluation.

Incapacitance tester is a device allowing assessing changes in hind paw weight distribution between the right (osteoarthritic) and left (contralateral control) limbs. It has been utilized as an index of joint discomfort and may be useful for the discovery of novel pharmacologic agents in human osteoarthritis. The animals were assessed prior to surgery as well as 24 hours after surgery for the relative amount of weight bearing on either knee using a Linton Incapacitance meter (Linton Instrumen-tation, Norfolk, UK). The animals were ranked according to the difference between the right limb and the left limb weight bearing. The experimental versus control knees were then determined so that there was similar distribution of right-limbed versus left-limbed animals. This step is important in order to prevent bias related to animal "handedness." Animals were examined again two weeks after injection of the intra-articular therapy. The animals were examined again 14 days after instillation of the intra-articular therapeutic agent.

Histological Evaluation.

The rats were euthanized using intraperitoneal 200 mg/kg sodium pentobarbital injection. The knees were dissected out and processed for routine histology following fixation with 1% cetylpyridinium chloride—4% formalin solution for 48 hours. Decalcification was carried out in EDTA for three weeks on average. Masson's trichrome and hematoxylin stains were evaluated. The following parameters were measured: cartilage thickness at the lowest part of the medial femoral condyle, osteophyte formation, cyst formation, and subchondral bone plate thickness. Quantitative histology was performed using an image analysis program (ImageJ). Statistical analysis was performed using the Microsoft Excel add-in program Analyze-it version 2.22.

Results

All animals survived the surgery, and their joint did not exhibit any evidence of inflammation or wound breakdown. Weight gain proceeded as expected. Incapacitance Tester Evaluation revealed that the difference between the experimental and control knee averaged 1±2 grams prior to surgery. The relative weight-bearing did not significantly changed following meniscectomy (2±2). After 2 weeks, the amount of weight bearing was measured again. The animals bore weight preferentially on the experimental knee (16.6±4 grams). This difference was found to be significant as compared to the measurement 24 hours following surgery (Student's t-test, $P<0.017$).

Figure 13:
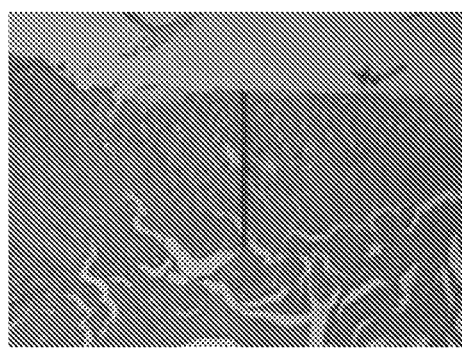
FIG. 13 shows histology micrographs presenting rat knees following medial meniscectomy which were further treated with a composition comprising chitosans and hyaluronate (panel a) or with control (panel b).
Figure 13:

Histological Evaluation revealed that cartilage thickness was significantly (Student's t-test. $P<0.043$) increased in the experimental groups (170±8) as compared with the control knees (108±10) (FIG. 13).

Figure 14:
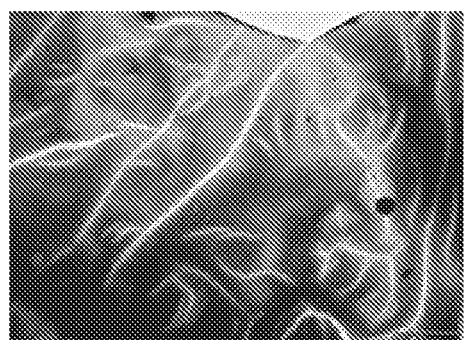
FIG. 14 shows micrographs of environmental scanning electron microscopy of a composition comprising chitosans and hyaluronate (panel a) or a composition comprising chitosans only (panel b).
Figure 14:
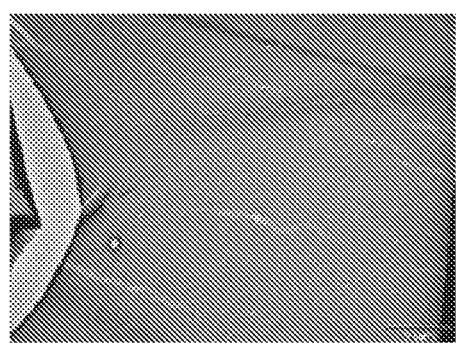
Figure 15:
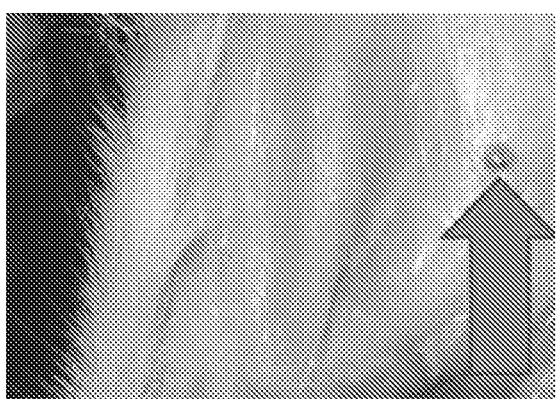
FIG. 15 presents micrographs showing that subcutaneous injection in rats of a chitosan composition comprising hyaluronate does not evoke an inflammatory response. The gel forms a discrete nodule (arrow); original magnification ×10.
Figure 15:

The hybrid gel appears to undergo self-assembly perhaps due to hyaluronate molecules aligning the smaller chitosan molecules (FIG. 14) and does not seem to induce an inflammatory response when injected subcutaneously in rats (FIG. 15). Cyst grading was performed using a 4-point scale, wherein means no cyst; 1 means minimal cyst; 2 means large cyst; and 3 means very large cyst. There were no cysts formed in the experimental group (average grade 0), while in the control group the average was 0.55±0.5. This difference was found to be significant (Student's t-test, $P<0.047$).

Subchondral bone plate thickness results showed no significant difference between the groups. Osteophyte grading was performed using a 4-point scale, wherein 0 means no osteophyte; 1 means minimal osteophyte; 2 means large soft tissue osteophyte; and 3 means large bony osteophyte. Average grade in the chitosan group was 0.8±0.5, while in the control group it was 1.2±0.3.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification and in addition, U.S. Pat. No. 8,153,612, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A chitosan composition which forms a hydrogel at near physiological pH and at 37° C., comprising at least one acetylated chitosan having a degree of acetylation in the range of from about 30% to about 60%, and at least one deacetylated chitosan having a degree of deacetylation that is about 70% to about 95%, the composition being in the form of an aqueous solution at neutral pH, wherein the ratio of said acetylated chitosan to said deacetylated chitosan in the composition is in the range of 1:1 to 4:1.

2. The chitosan composition of claim 1, further comprising at least one negatively charged polysaccharide.

3. The chitosan composition of claim 2, wherein the negatively charged polysaccharide is hyaluronic acid.

4. The chitosan composition of claim 1, further comprising acetylglucosamine oligomers.

5. The chitosan composition of claim 4, wherein the acetylglucosamine oligomers comprise Tri-N-acetyl-glucosamine.

6. The chitosan composition of claim 4, wherein the acetylglucosamine oligomers are present in the composition at a concentration of between 0.05% to 10% w/v.

7. The chitosan composition of claim 1, further comprising a cross-linking agent in an amount sufficient to accelerate gelation of the chitosan composition.

8. The chitosan composition of claim 7, wherein said cross-linking agent is capable of cross-linking the amine or hydroxyl residues of the chitosans.

9. The chitosan composition of claim 7, wherein said amount of the cross linking agent is in the range of between 0.1% to 2% w/v.

10. The chitosan composition of claim 7, wherein the cross-linking agent is added to the chitosan composition prior to introducing said chitosan composition into a site in vivo.

11. The chitosan composition of claim 7, wherein the cross-linking agent is genipin.

12. A process for preparing a stable pH-dependent and temperature-dependent chitosan hydrogel composition comprised of at least one acetylated chitosan having a degree of acetylation of from about 30% to about 60%, and at least one deacetylated chitosan having a degree of deacetylation that is about 70% to about 95%, which process comprises:
  d) dissolving said acetylated chitosan and said deacetylated chitosan in an acidic aqueous solution at a temperature between 0° C. to 10° C., to thereby form a composite solution, wherein the ratio of said acetylated chitosan and said deacetylated chitosan in said composite solution is in the range of 1:1 to 4:1;
  e) adjusting the pH of said composite solution to a value of 6.6 to 7.4 at a temperature between 0° C. to 10° C.; and
  f) increasing at least one of the temperature of said composite solution to about 37° C. and/or raising the pH to physiological pH.

13. The process of claim 12, further comprising adding a negatively charged polysaccharide to the composition before step c.

14. The process of claim 13 wherein the polysaccharide is hyaluronic acid.

15. The process of claim 12, further comprising adding acetylglucosamine oligomers to the composition.

16. The process of claim 12, further comprising adding a cross-linking agent in an amount sufficient to accelerate gelation of the chitosan composition, wherein the cross-linking agent is added to the composition prior to introducing said chitosan composition into a site in vivo.

17. The process of claim 16 wherein the cross-linking agent is genipin.

18. A hydrogel chitosan composition formed by the process of claim 12.

19. A method of treating medical condition in a subject in need thereof, comprising applying into a site of the medical condition a chitosan composition comprising at least one acetylated chitosan having a degree of acetylation in the range of from about 30% to about 60%, and at least one deacetylated chitosan having a degree of deacetylation that is about 70% to about 95%, the composition being in the form of an aqueous solution at neutral pH, wherein the ratio of said acetylated chitosan to said deacetylated chitosan in the solution is in the range of 1:1 to 4:1.

20. The method of claim 19, wherein the medical condition is selected from the group consisting of: osteoarthritis, fracture repair, bone structural support, cartilage repair, intervertebral disc repair, meniscal repair, bone reconstruction, bone filling and synovial fluid replacement.

21. A kit for producing a chitosan hybrid hydrogel, comprising:
  (i) a container containing a chitosan composition comprising at least one acetylated chitosan having a degree of acetylation in the range of from about 30% to about 60%, and at least one deacetylated chitosan having a degree of deacetylation that is about 70% to about 95%, wherein the ratio of said acetylated chitosan to said deacetylated chitosan in the solution is in the range of 1:1 to 4:1;
  (ii) a container containing a cross-linking agent in an amount sufficient to accelerate gelation of the chitosans; and
  (iii) instructions for preparing the chitosan hybrid hydrogel.

22. The kit of claim 21, wherein the container containing a chitosan composition further comprises a negatively charged polysaccharide.

23. The kit of claim 22, wherein the polysaccharide is hyaluronic acid.

24. The kit of claim 21, wherein the container containing a chitosan composition further comprises acetylglucosamine oligomers.

25. The kit of claim 24, wherein the acetyl glucosamine oligomers comprise Tri-N-acetyl-glucosamine.

26. The kit of claim 21, wherein the kit further comprises a container containing a solvent for dissolving the cross-linking agent.

* * * * *

UNITED STATES PATENT AND TRADEMARK OFFICE
CERTIFICATE OF CORRECTION

PATENT NO.         : 9,034,348 B2                                    Page 1 of 1
APPLICATION NO.    : 13/830268
DATED              : May 19, 2015
INVENTOR(S)        : Ben-Shalom et al.

It is certified that error appears in the above-identified patent and that said Letters Patent is hereby corrected as shown below:

In the Claims

<u>Column 31, Claim 12</u>
Line 50, before "dissolving", delete "d)" and insert -- a) --.
Line 56, before "adjusting", delete "e)" and insert -- b) --.
Line 58, before "increasing", delete "f)" and insert -- c) --.

Signed and Sealed this
Eighth Day of September, 2015

Michelle K. Lee
*Director of the United States Patent and Trademark Office*